(12) United States Patent
Qiao et al.

(10) Patent No.: US 10,669,598 B2
(45) Date of Patent: *Jun. 2, 2020

(54) CATALYTIC BIOMASS DECONSTRUCTION

(71) Applicant: VIRENT, INC., Madison, WI (US)

(72) Inventors: Ming Qiao, Pewaukee, WI (US);
Randy D. Cortright, Madison, WI (US); Dick A. Nagaki, The Woodlands, TX (US); Elizabeth Woods, Middleton, WI (US)

(73) Assignee: VIRENT, INC., Madison, WI (US)

( * ) Notice: Subject to any disclaimer, the term of this patent is extended or adjusted under 35 U.S.C. 154(b) by 326 days.

This patent is subject to a terminal disclaimer.

(21) Appl. No.: 15/246,148

(22) Filed: Aug. 24, 2016

(65) Prior Publication Data

US 2016/0362756 A1 Dec. 15, 2016

Related U.S. Application Data

(63) Continuation of application No. 13/339,553, filed on Dec. 29, 2011, now abandoned.

(60) Provisional application No. 61/428,454, filed on Dec. 30, 2010.

(51) Int. Cl.
| | |
|---|---|
| *C13K 1/02* | (2006.01) |
| *B01J 23/42* | (2006.01) |
| *B01J 23/46* | (2006.01) |
| *B01J 31/10* | (2006.01) |
| *C07C 29/132* | (2006.01) |
| *C07C 45/55* | (2006.01) |
| *C07C 27/04* | (2006.01) |
| *C10L 1/02* | (2006.01) |
| *C07C 29/00* | (2006.01) |
| *C07C 51/00* | (2006.01) |
| *C07D 307/46* | (2006.01) |

(52) U.S. Cl.
CPC .......... *C13K 1/02* (2013.01); *B01J 23/42* (2013.01); *B01J 23/462* (2013.01); *B01J 31/10* (2013.01); *C07C 27/04* (2013.01); *C07C 29/00* (2013.01); *C07C 29/132* (2013.01); *C07C 45/55* (2013.01); *C07C 51/00* (2013.01); *C07D 307/46* (2013.01); *C10L 1/02* (2013.01); *C10L 1/026* (2013.01); *C10G 2300/1011* (2013.01); *C10G 2300/1014* (2013.01); *C10G 2300/202* (2013.01); *C10G 2300/4081* (2013.01); *C10G 2300/44* (2013.01); *C10G 2300/805* (2013.01); *Y02P 30/20* (2015.11)

(58) Field of Classification Search
CPC ......... C13K 1/02; C07C 29/132; C07C 45/55; C07C 51/00; C07D 307/46; B01J 23/462; B01J 23/42; B01J 31/10
USPC ............................................................ 127/37
See application file for complete search history.

(56) References Cited

U.S. PATENT DOCUMENTS

| | | | | |
|---|---|---|---|---|
| 8,642,813 | B2 * | 2/2014 | Qiao ................. | C13K 1/02 |
| | | | | 568/22 |
| 9,045,383 | B2 * | 6/2015 | Qiao ................. | B01J 23/687 |
| 2008/0300435 | A1 * | 12/2008 | Cortright ............ | C10G 3/45 |
| | | | | 585/14 |

OTHER PUBLICATIONS

Yu et al. Some Recent Advances in Hydrolysis of Biomass in Hot-Compressed Water and Its Comparisons with Other Hydrolysis Methods. Energy & Fuels 2008, 22, 46-60. (Year: 2008).*
Zakzeski et al., Chem. Rev. 110:3552-3599, 2010.
Alonso et al., Green Chemistry, 12:1493-1513, 2010.

* cited by examiner

*Primary Examiner* — Yih-Horng Shiao
(74) *Attorney, Agent, or Firm* — Quarles & Brady LLP

(57) ABSTRACT

The present invention provides processes for catalytically converting biomass to oxygenated compounds suitable for use in bioreforming processes.

31 Claims, 23 Drawing Sheets

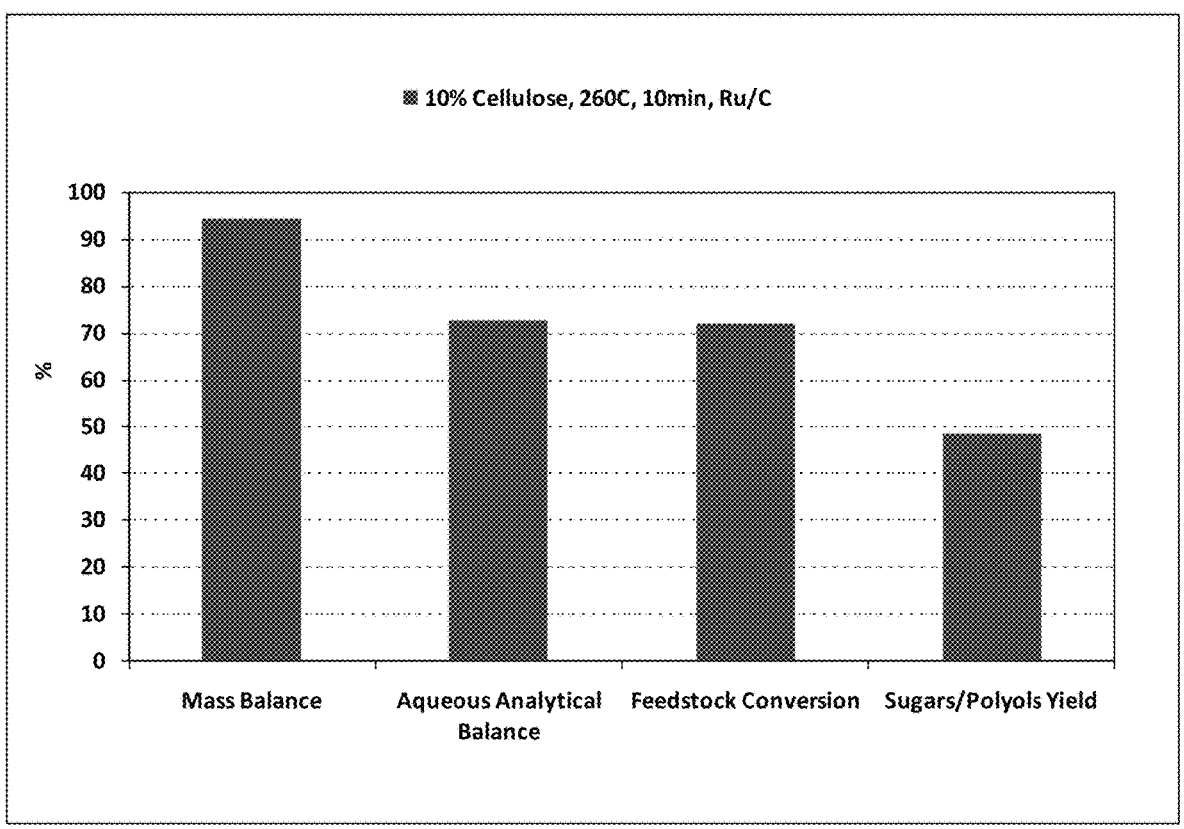
Fig. 2. Microcrystalline cellulose conversion data.

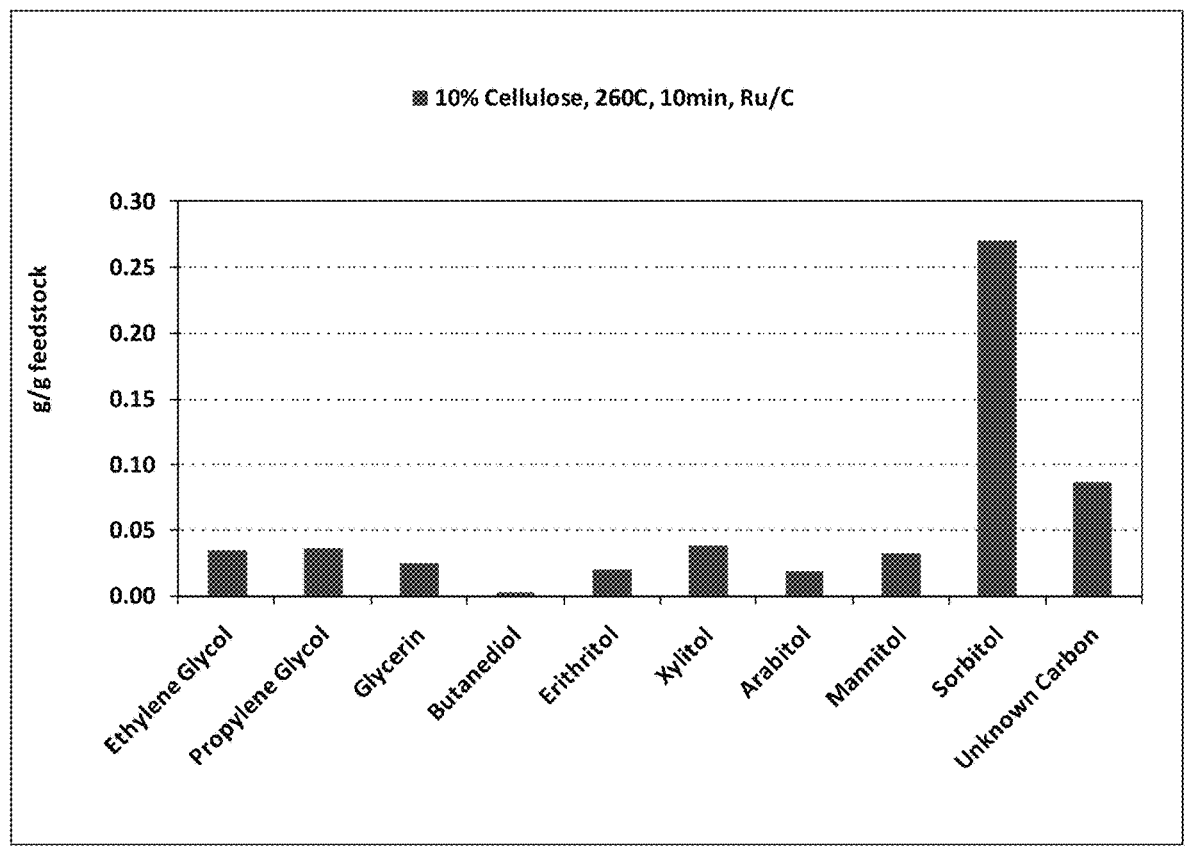
Fig. 3. Product Yields in aqueous fraction from MCC

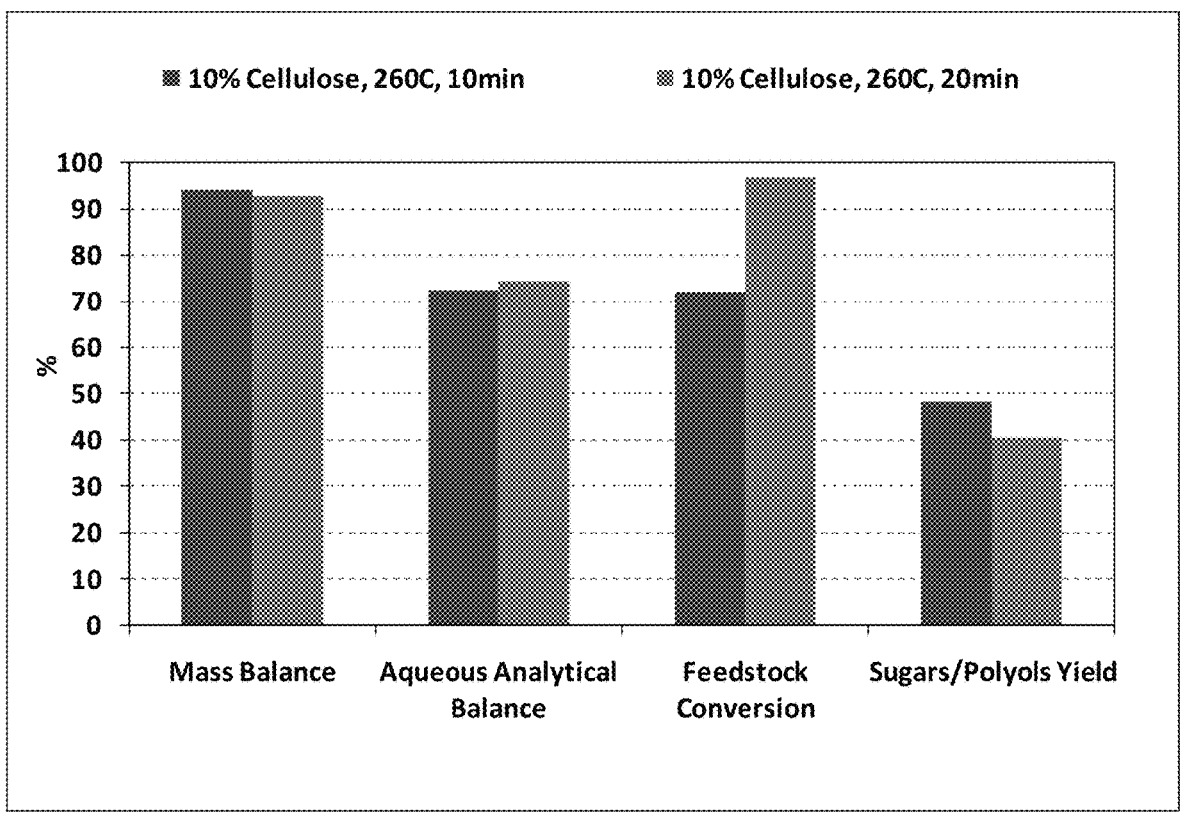
Fig. 4. 10 minute vs. 20 minute conversion data

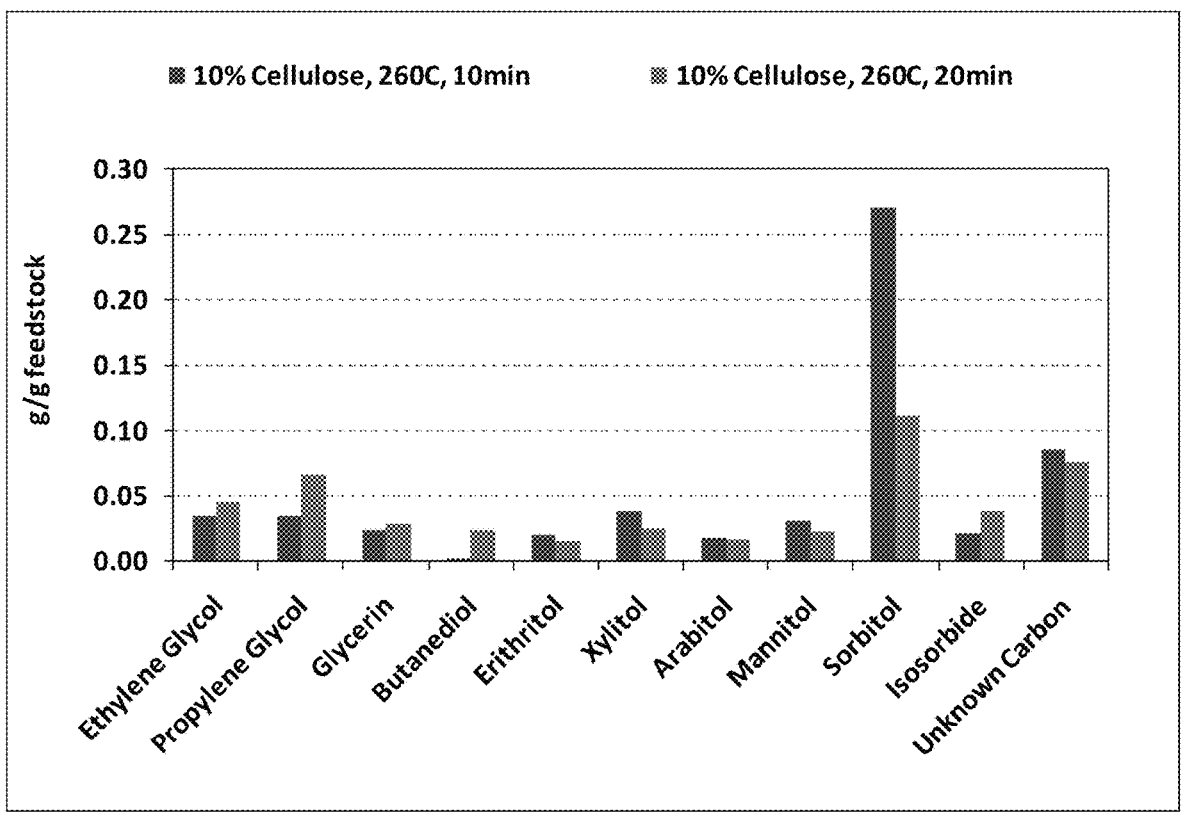
Fig. 5. Product yields in aqueous from MCC

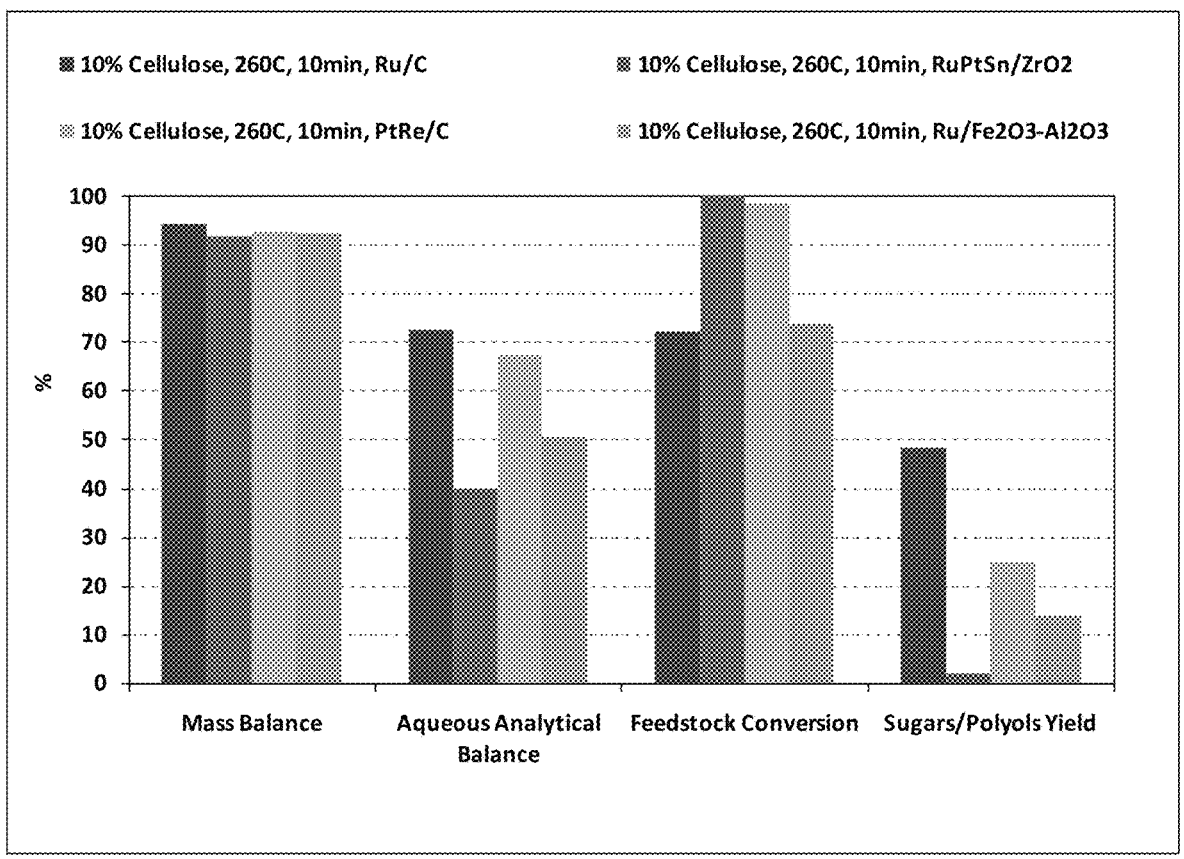
Fig. 6. Conversion of MCC using various deconstruction catalysts

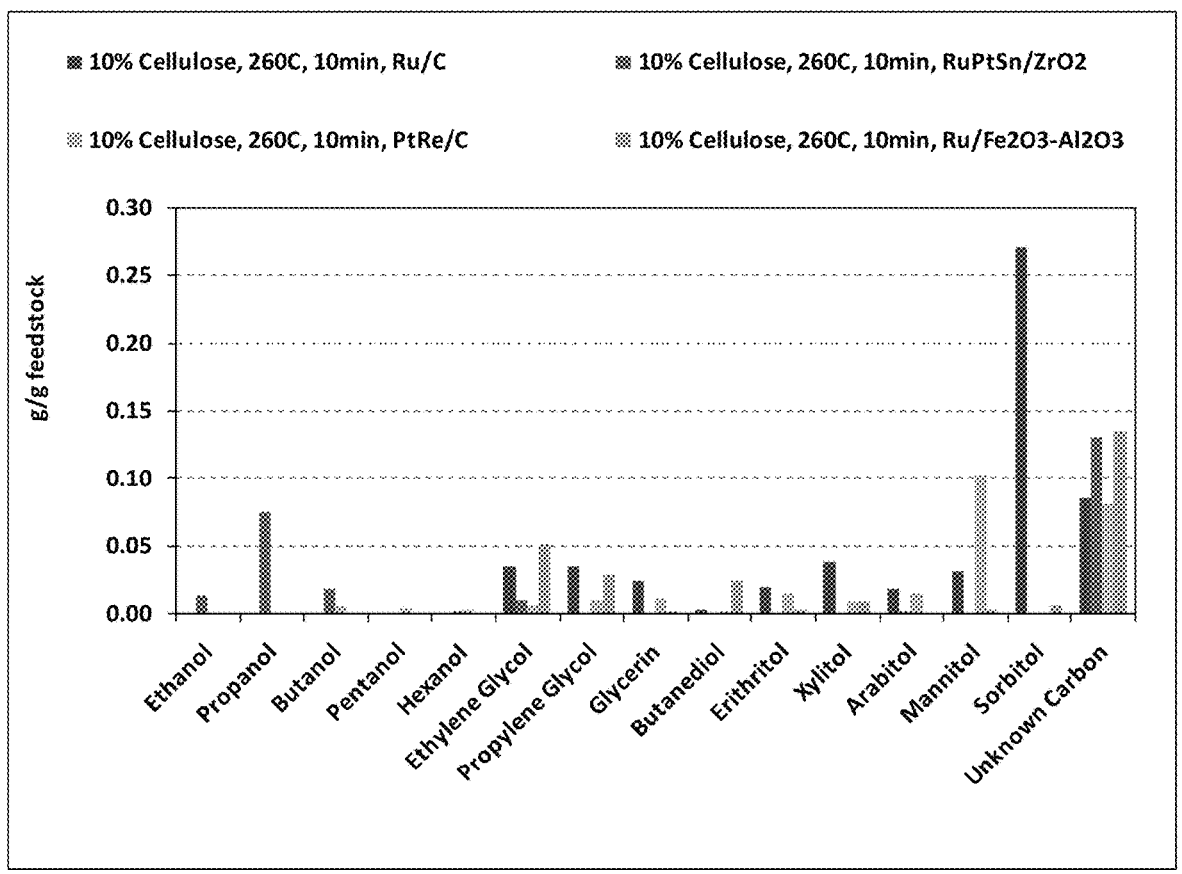
Fig. 7. Product yields from the conversion of MCC using various deconstruction catalysts.

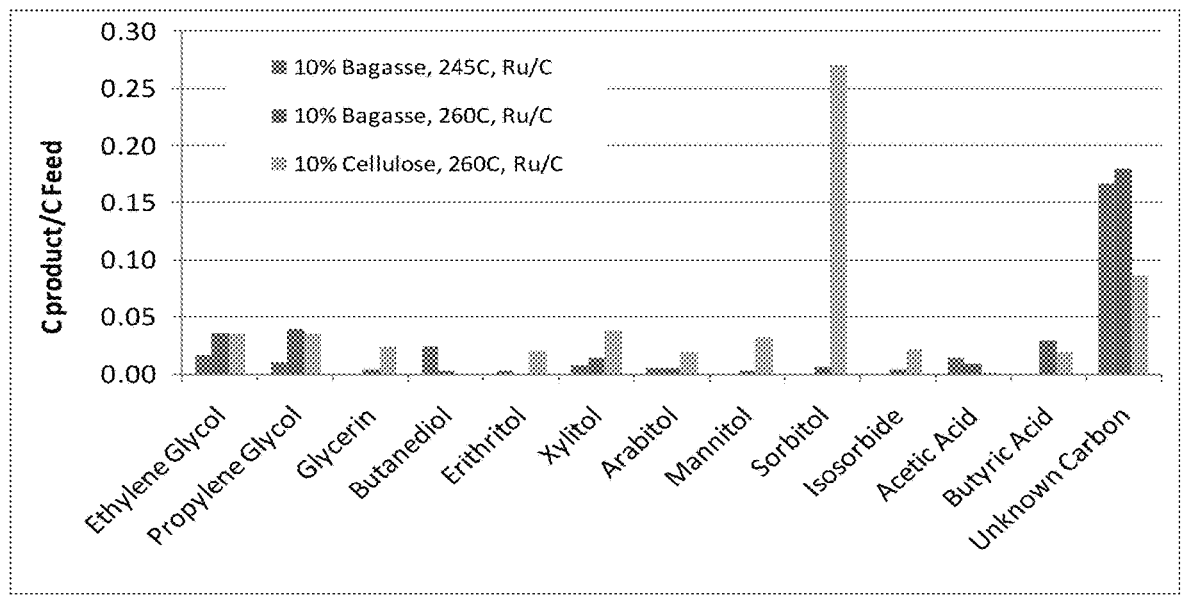
Fig. 8. Comparison of bagasse conversion and MCC conversion using Ru/C catalyst.
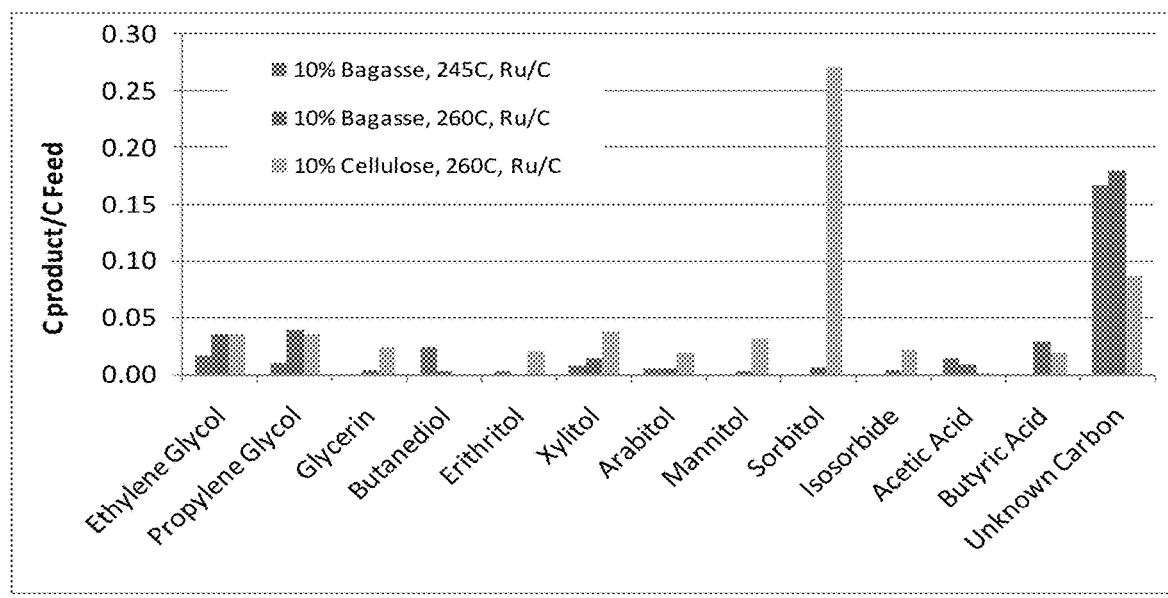
Fig. 9. Product yields comparing bagasse and MCC conversion using Ru/C catalyst.

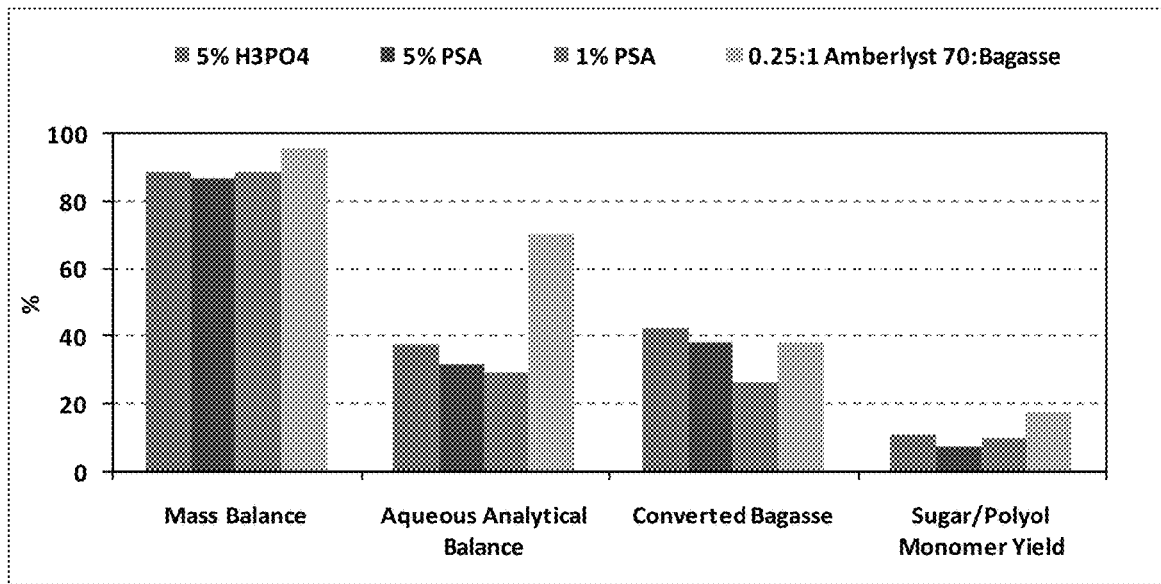
Fig. 10. Overall results of bagasse hydrolysis using phosphoric acid, PSA and Amberlyst 70.
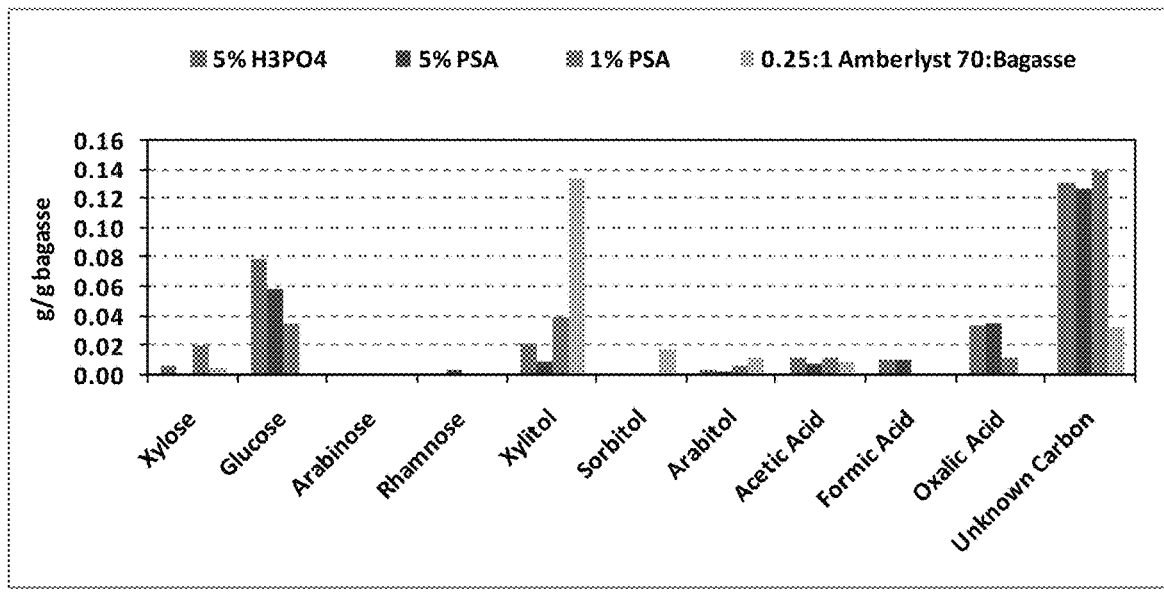
Fig. 11. Major products of bagasse hydrolysis using phosphoric acid, PSA and Amberlyst 70.

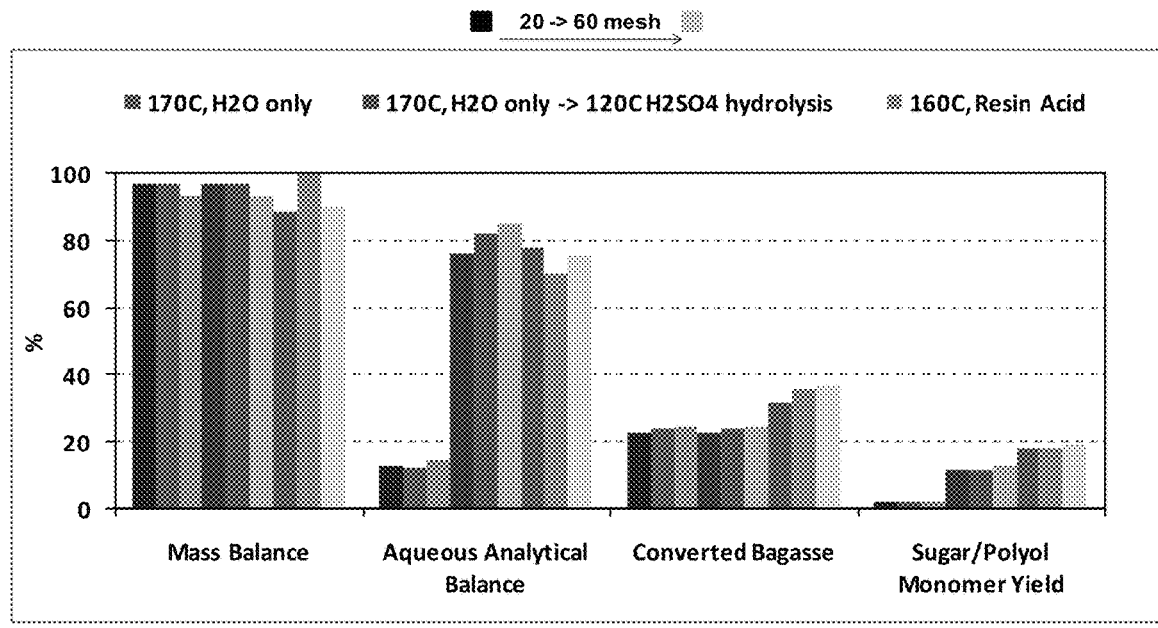
Fig. 12. Results of hydrolysis using different bagasse particle sizes (<20, 40, and 60 mesh).
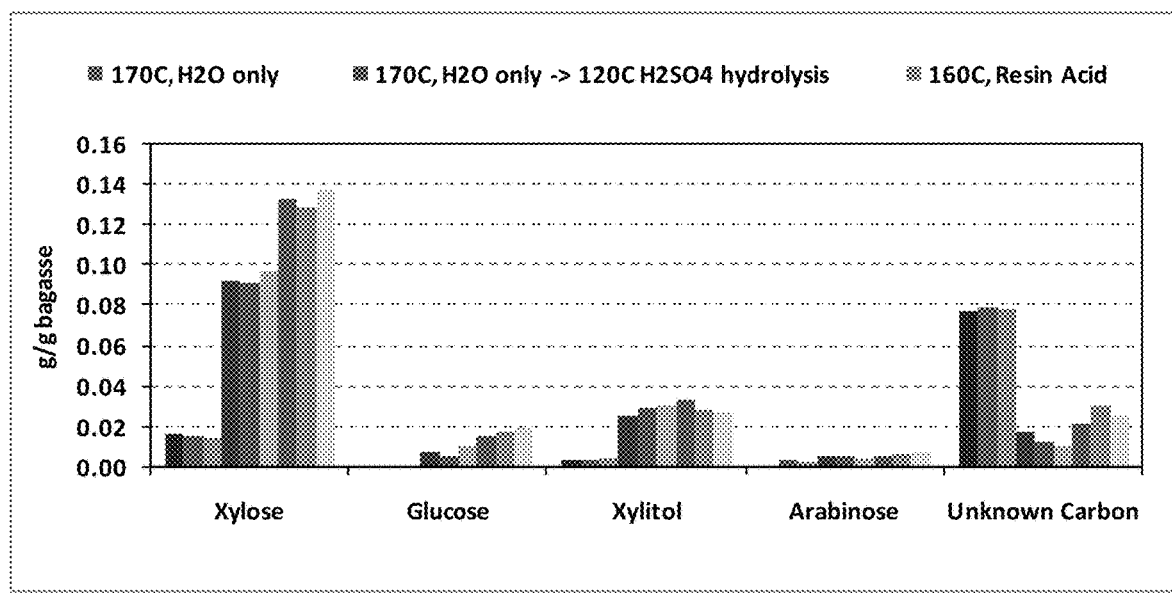
Fig. 13. Major products of hydrolysis using different bagasse particle sizes (<20, 40, and 60 mesh).

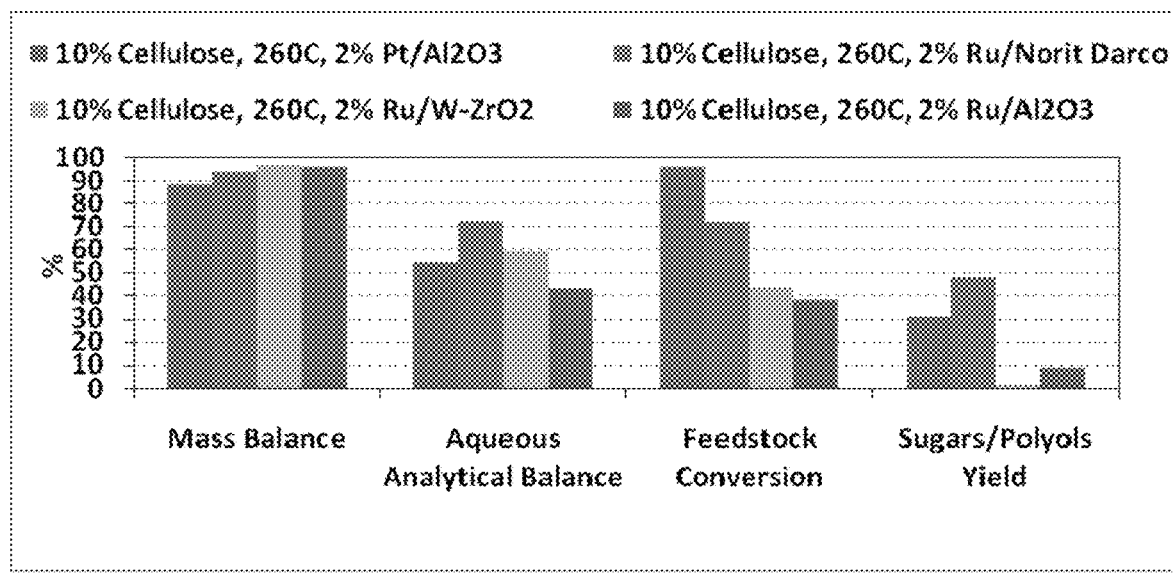
Fig. 14: Hydrogenolysis of microcrystalline cellulose with different catalysts.

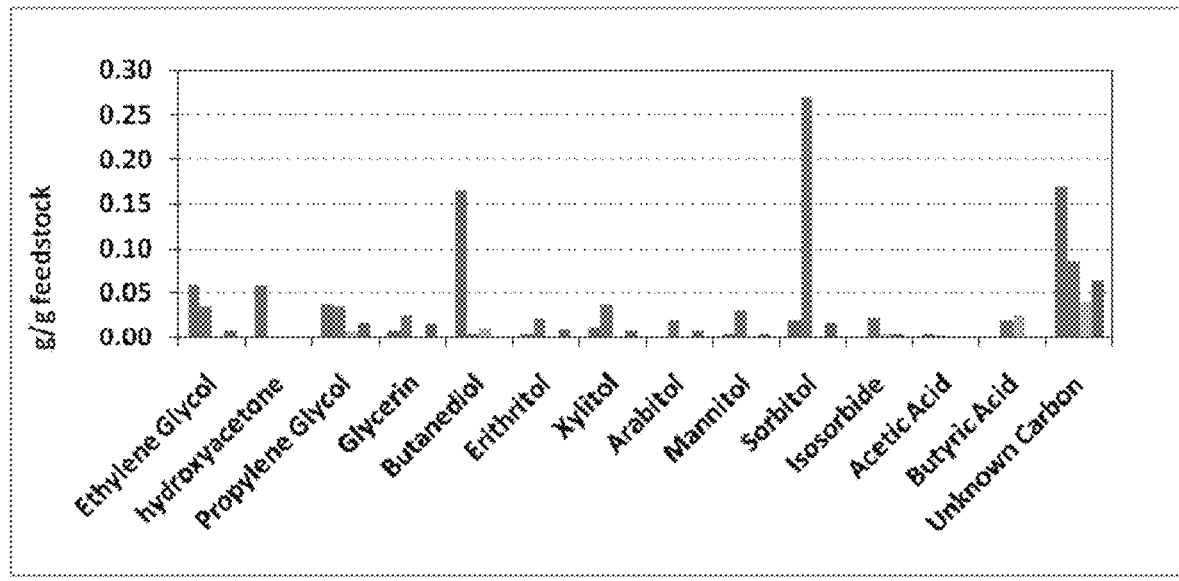
Fig. 15: Products of hydrogenolysis of microcrystalline cellulose with different catalysts.
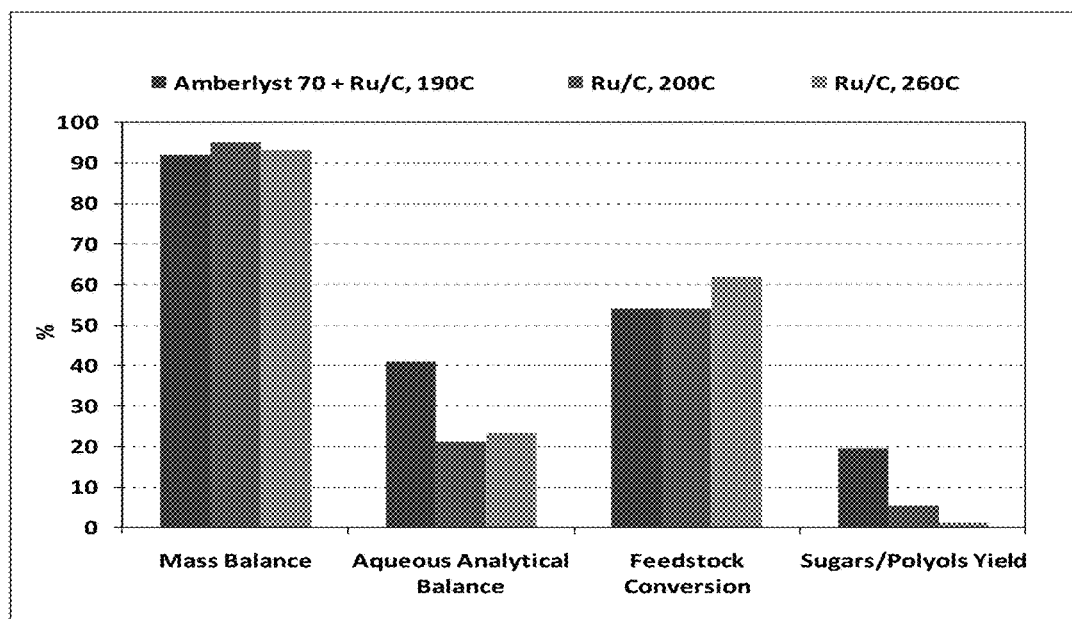
Fig. 16: Hydrogenolysis of corn fiber.

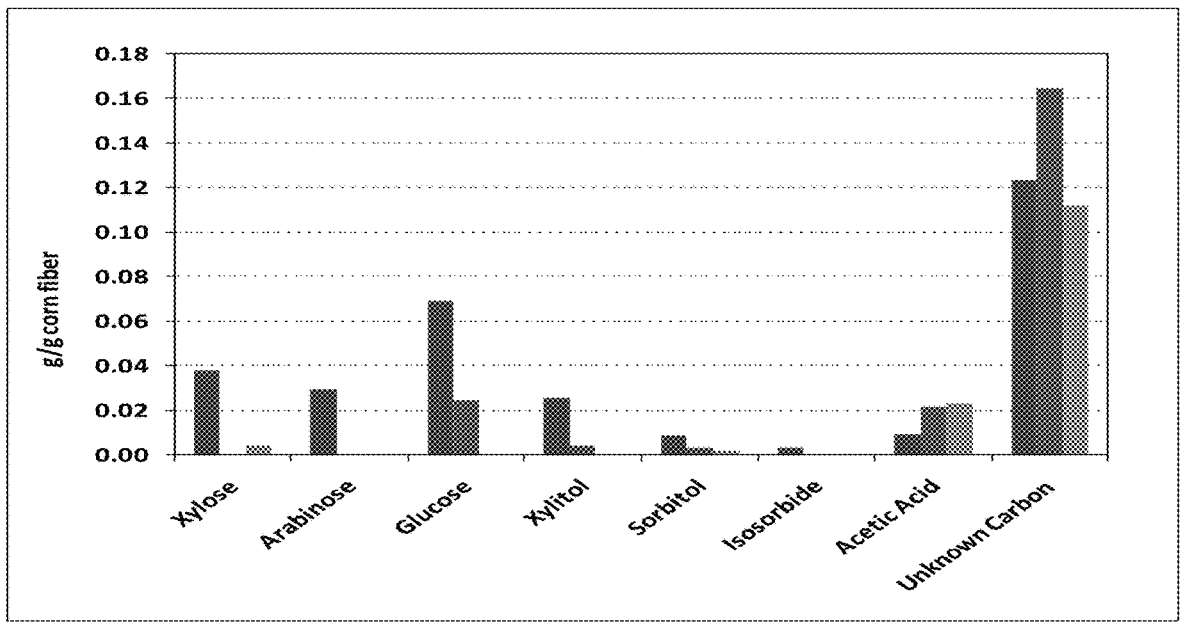
Fig. 17: Major products form hydrogenolysis of corn fiber.
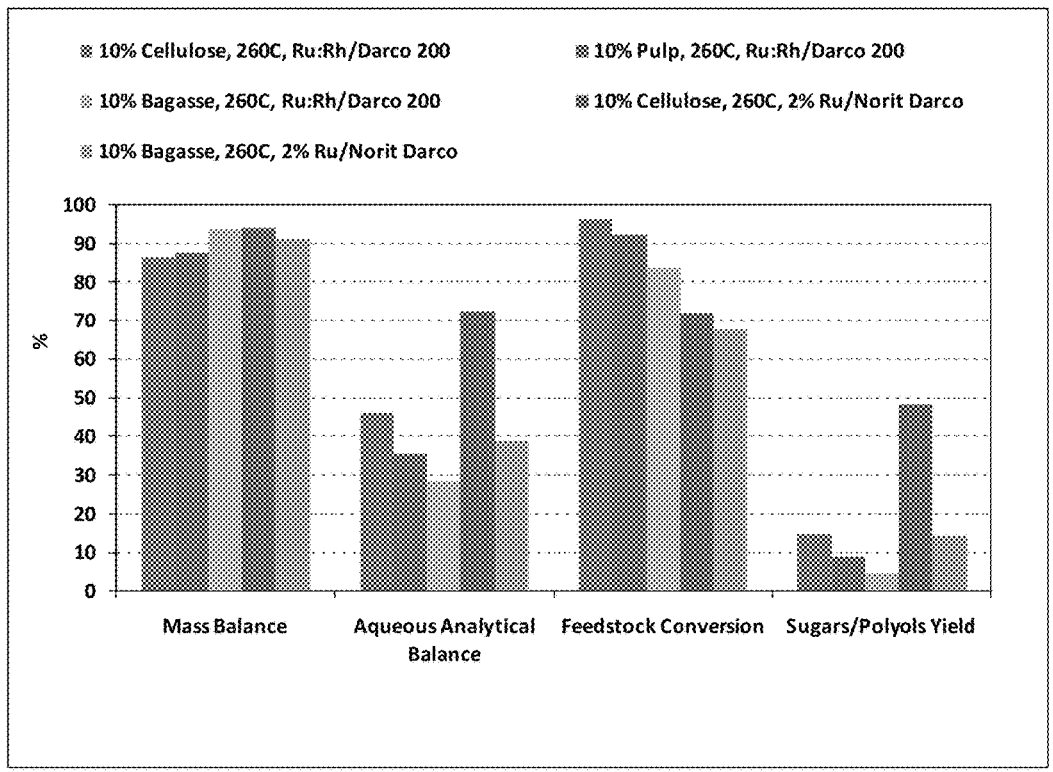
Fig. 18: Catalytic deconstruction of lignocellulosics.

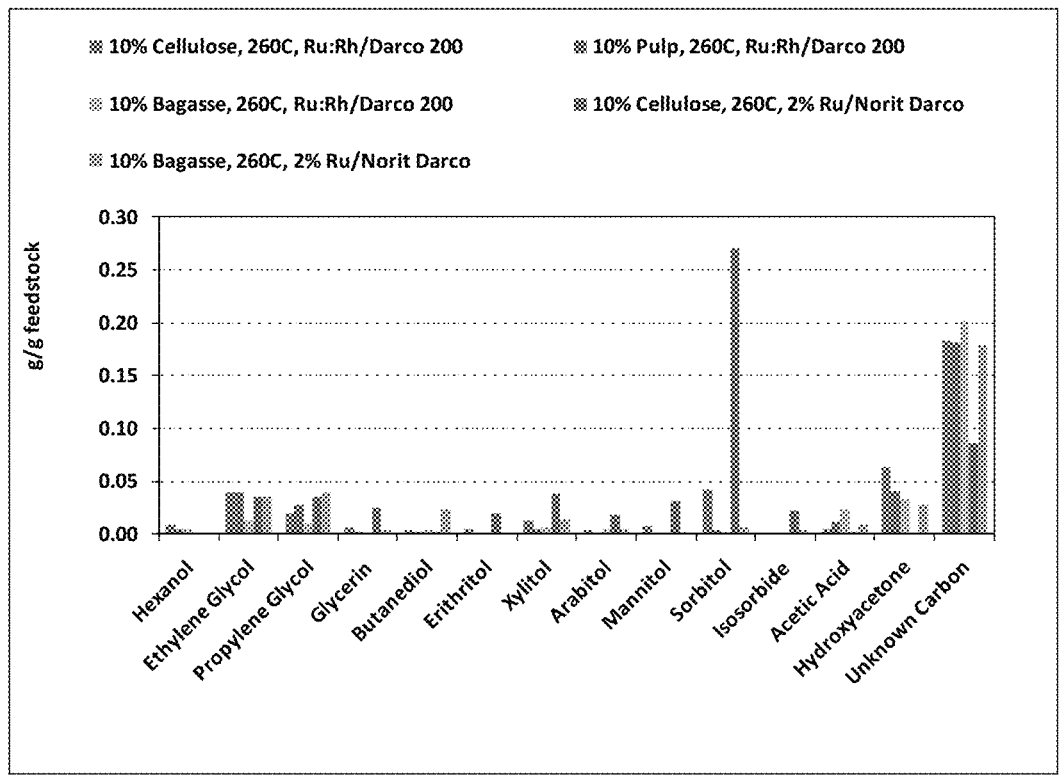
Fig. 19: Products in aqueous fraction resulting from biomass deconstruction.
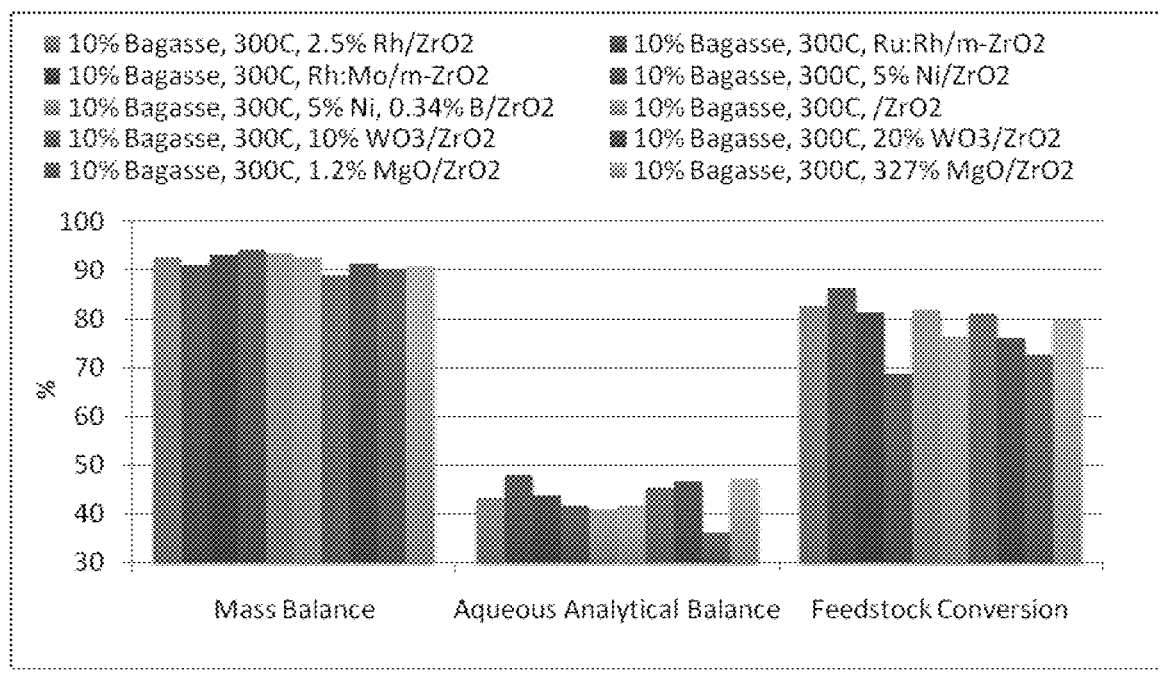
Fig. 20. Conversion of sugarcane bagasse over various catalysts.

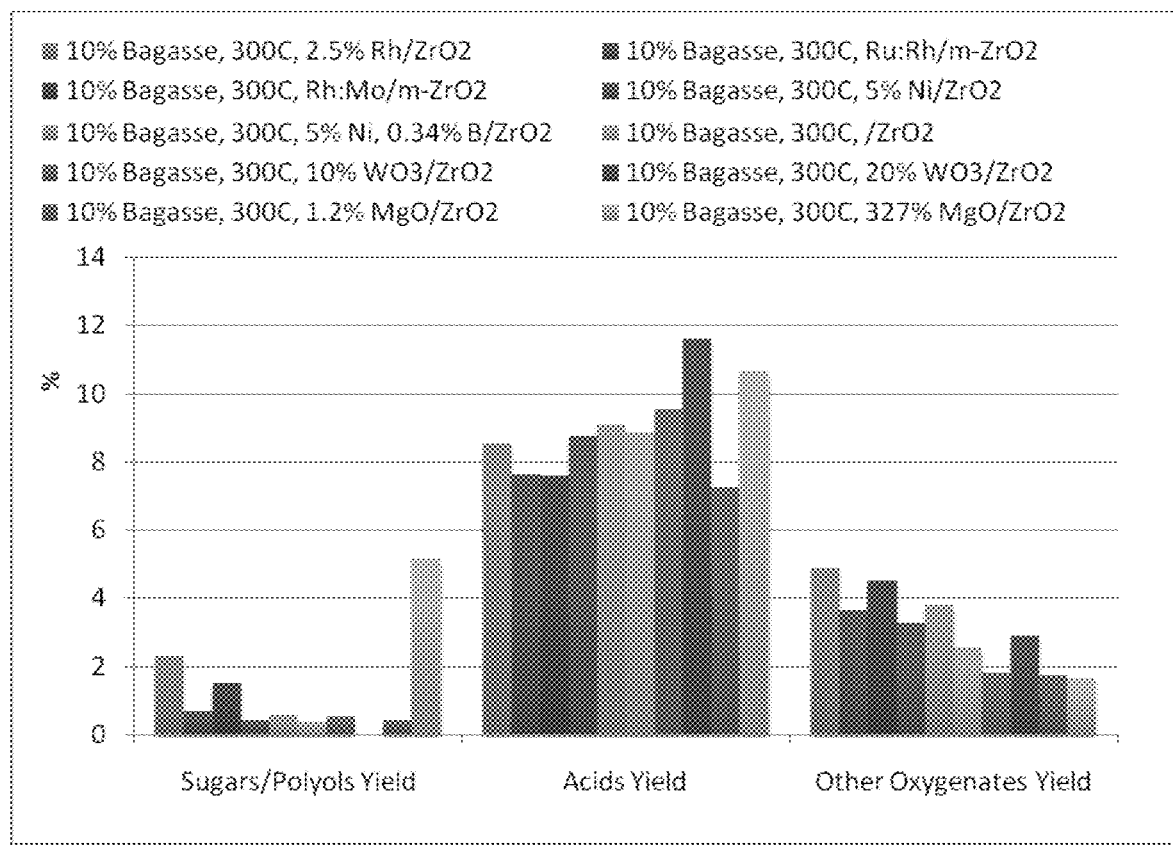
Fig. 21. Oxygenated product yields for the conversion of sugarcane bagasse over various catalysts.

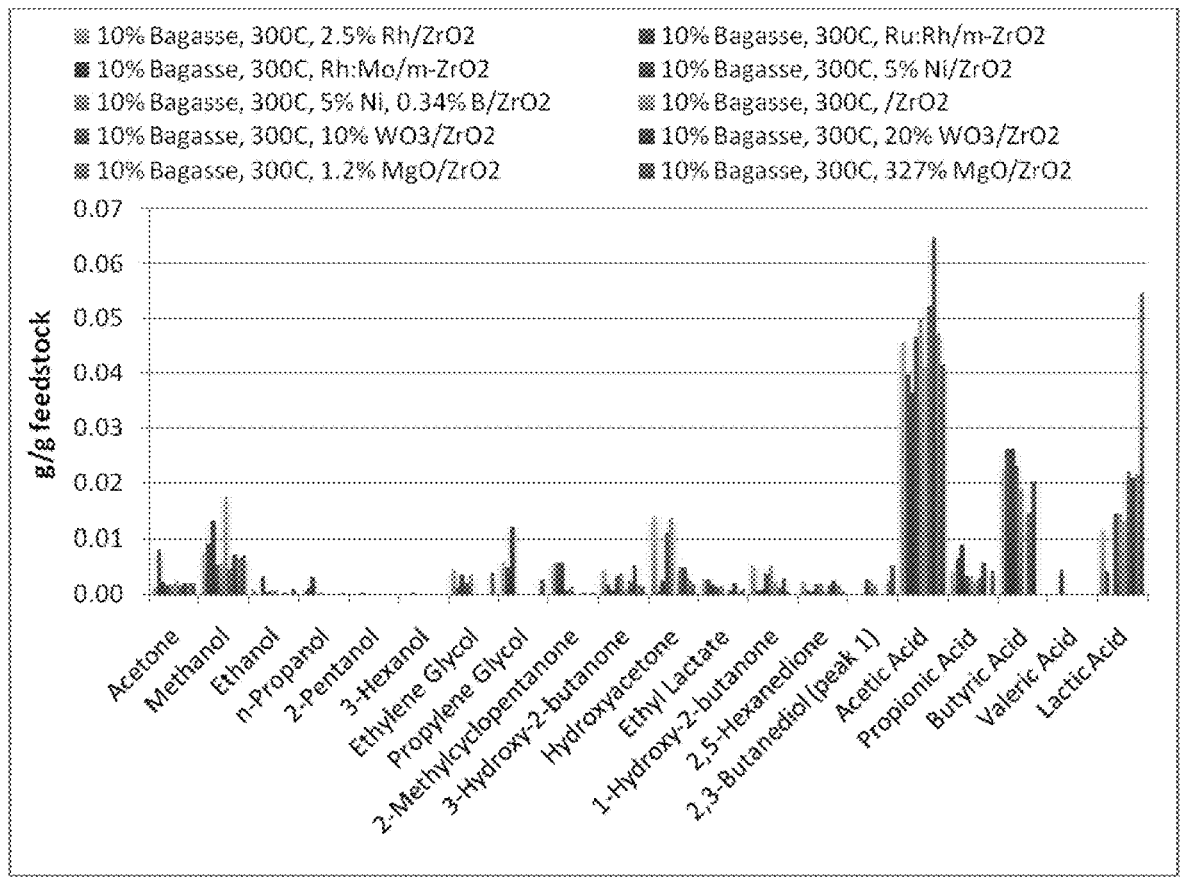
Fig. 22. Detailed product distribution of the conversion of sugarcane bagasse over various catalysts.
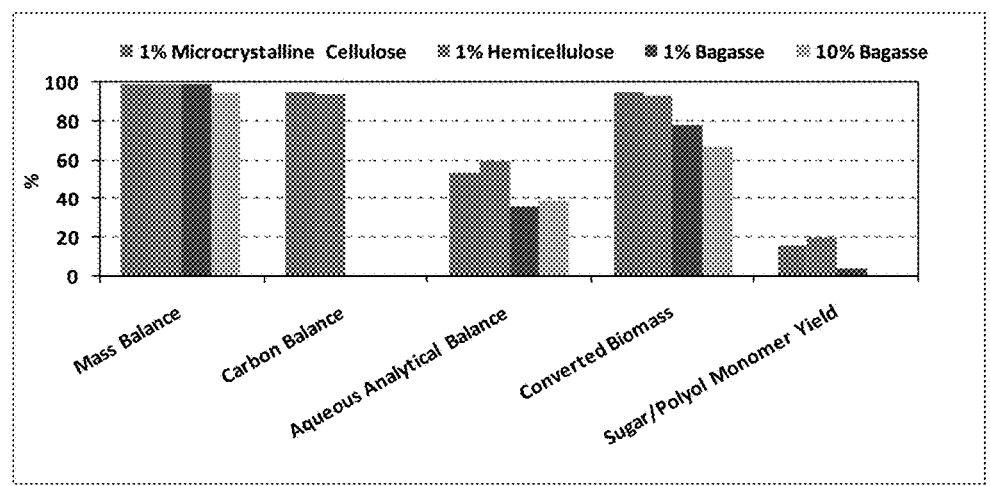
Fig. 23. Cellulosic conversion over nickel tungsten carbide catalyst

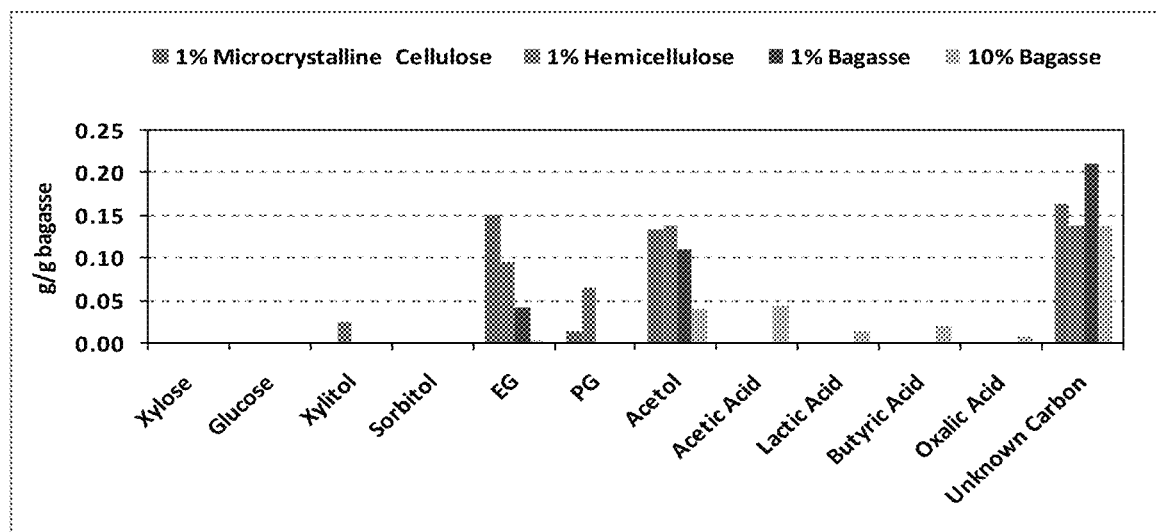
Fig. 24. Product distribution of cellulosics conversion over nickel tungsten carbide catalyst

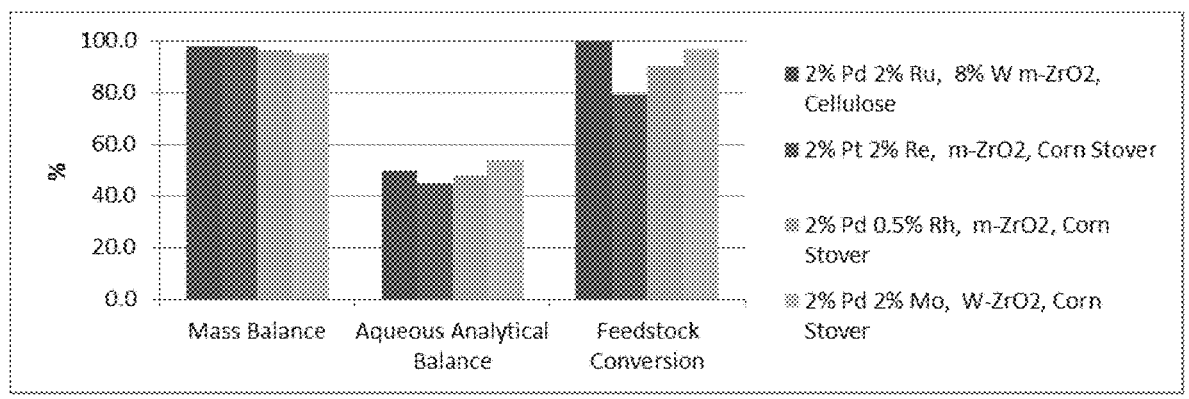
Fig. 26. Mass and Analytical Balances and Feedstock Conversion of Catalytic Deconstruction
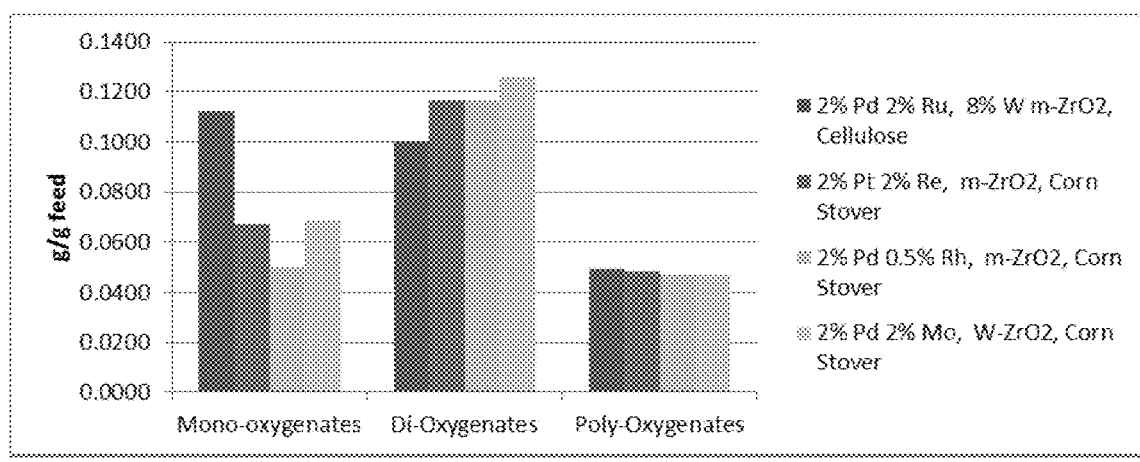
Fig. 27. Levels of Deoxygenation of Catalytic Deconstruction

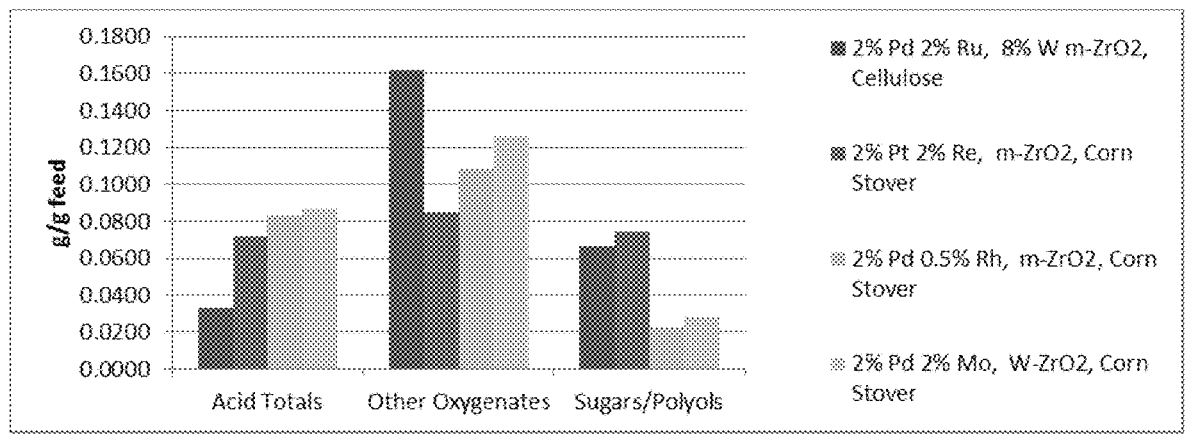
Fig. 28. Product Yields of Catalytic Deconstruction
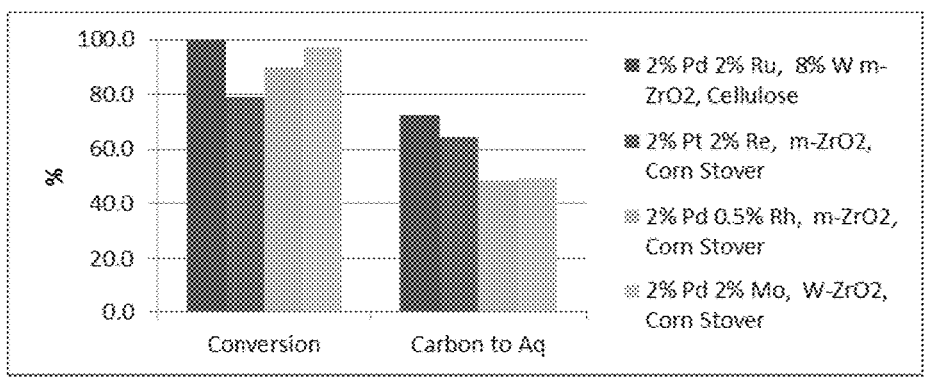
Fig. 29. Conversion and Conservation of Carbon of Catalytic Deconstruction

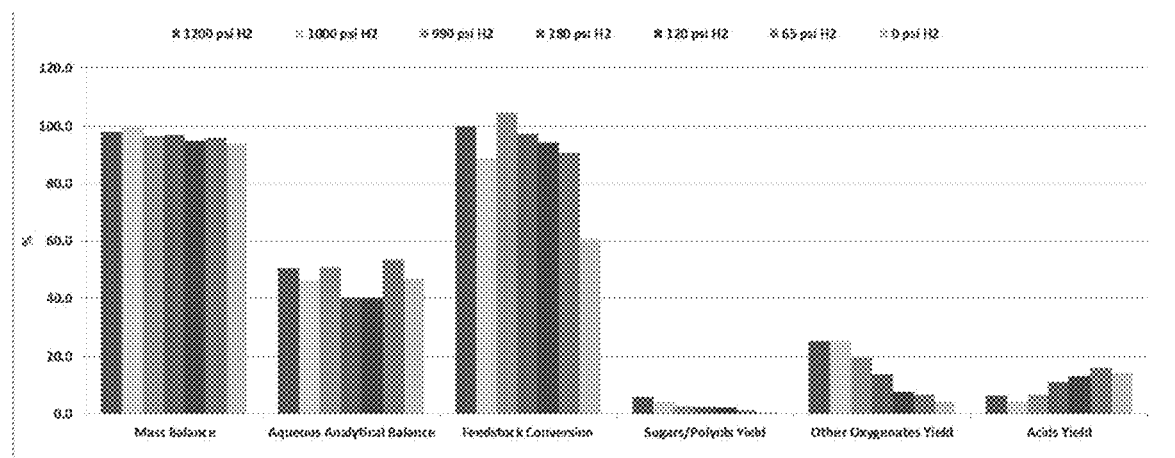
Fig. 30A. Carbon Conversion to the Aqueous Phase at Varying Reaction Hydrogen Partial Pressures with Microcrystalline Cellulose
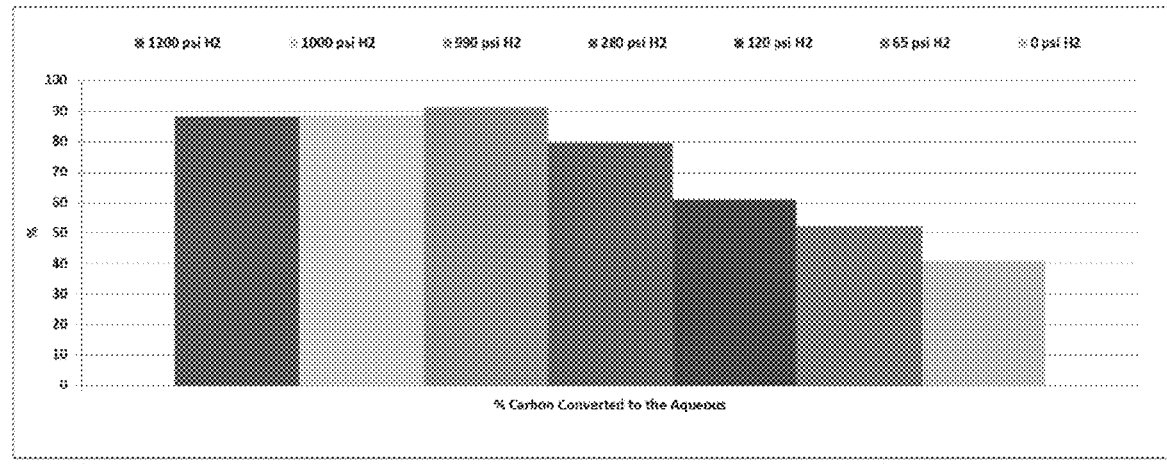
Fig. 30B. Carbon Conversion to Aqueous at Varying Reaction Hydrogen Partial Pressures with Microcrystalline Cellulose

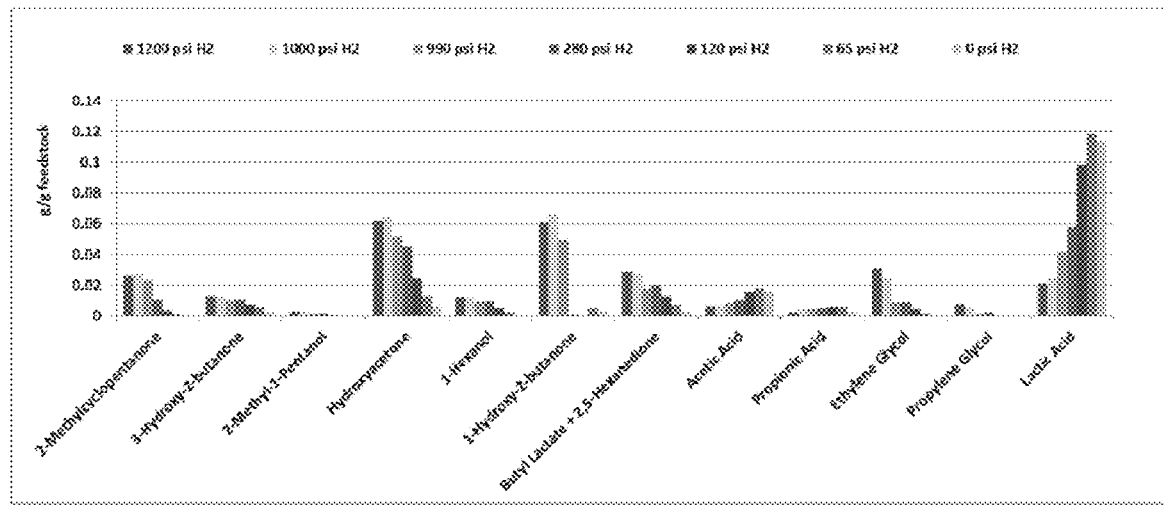
Fig. 31. Product Selectivity at Varying Reaction Hydrogen Partial Pressures with Microcrystalline Cellulose
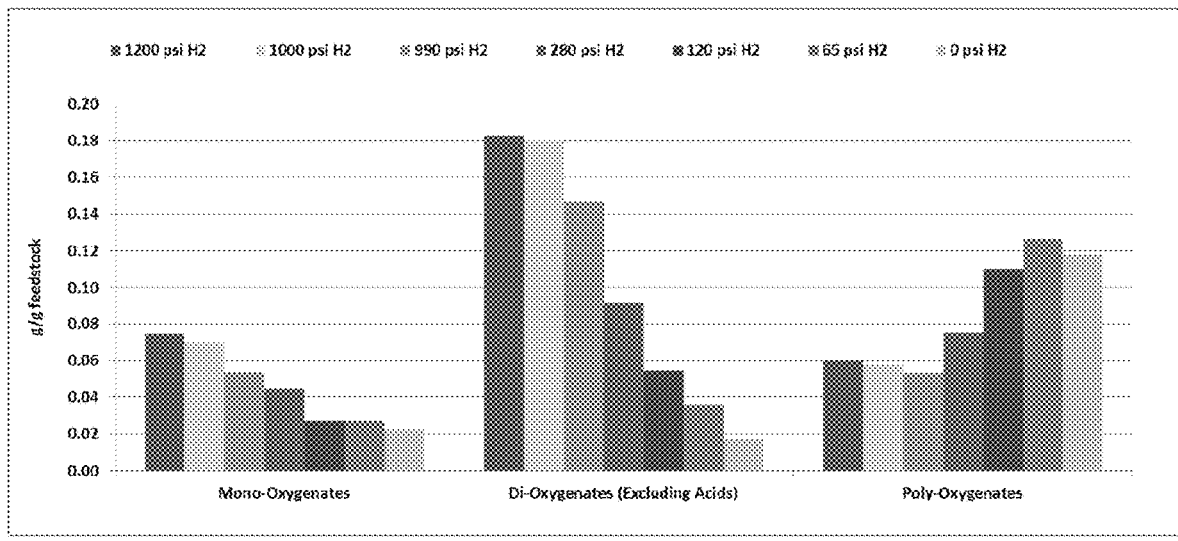
Fig. 32. Degree of Oxygenates at Varying Reaction Hydrogen Partial Pressures with Microcrystalline Cellulose

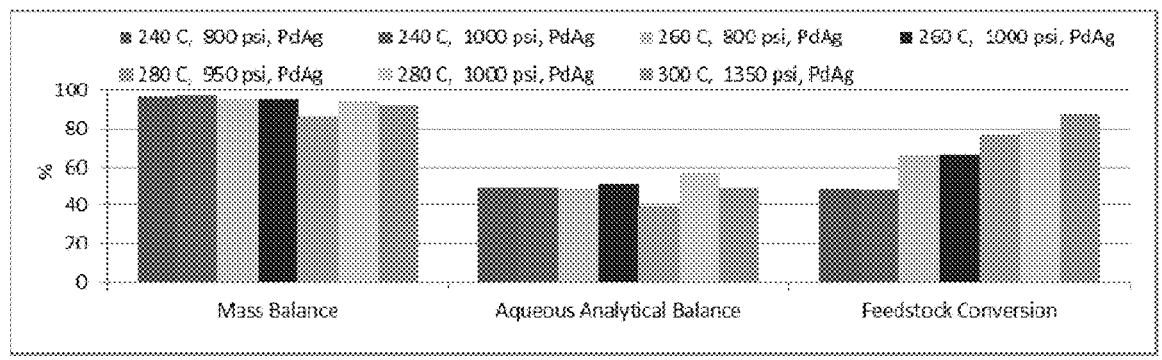
Fig. 33A. Overall Balances of Loblolly Pine Deconstruction at Varying Temperature and Pressure
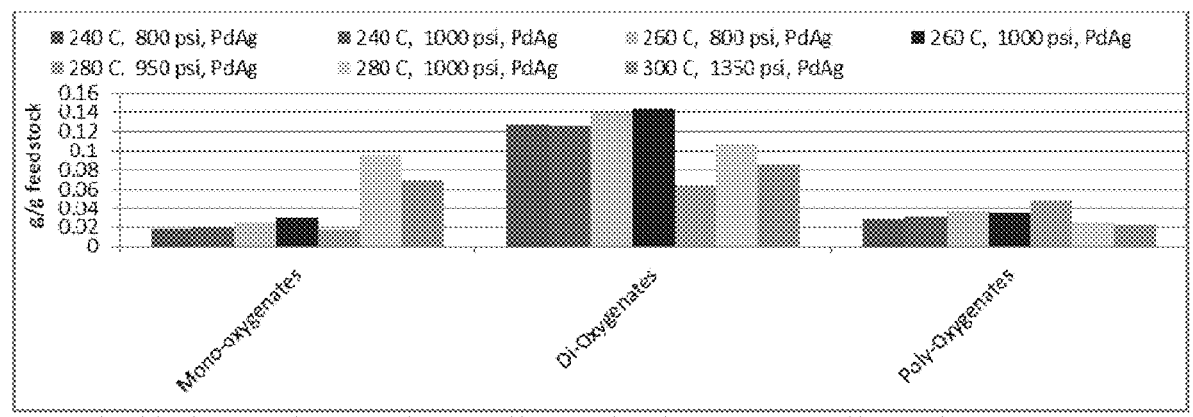
Fig. 33B. Biomass Conversion Results of Loblolly Pine Deconstruction at Varying Temperature and Pressure

CATALYTIC BIOMASS DECONSTRUCTION

CROSS-REFERENCE TO RELATED APPLICATION

This application is a continuation of U.S. application Ser. No. 13/339,553, filed Dec. 29, 2011, now pending, which claims the benefit of U.S. Provisional Application No. 61/428,454 filed on Dec. 30, 2010.

FEDERAL FUNDING STATEMENT

This invention was made with government support under award #70NANB7H7023, requisition #4700558 awarded by NIST through the ATP program. The government has certain rights in the invention.

TECHNICAL FIELD

The present invention is directed to catalysts and methods for deconstructing and fractionating biomass using heterogeneous catalysts.

BACKGROUND OF THE INVENTION

The increasing cost of fossil fuel and environmental concerns have stimulated world-wide interest in developing alternatives to petroleum-based fuels, chemicals, and other products. Biomass materials are a possible renewable alternative.

Lignocellulosic biomass includes three major components. Cellulose, a primary sugar source for bioconversion processes, includes high molecular weight polymers formed of tightly linked glucose monomers. Hemicellulose, a secondary sugar source, includes shorter polymers formed of various sugars. Lignin includes phenylpropanoic acid moieties polymerized in a complex three dimensional structure. The resulting composition of lignocellulosic biomass is roughly 40-50% cellulose, 20-25% hemicellulose, and 25-35% lignin, by weight percent.

No cost-effective process currently exists for efficiently converting cellulose, hemicellulose, and lignin to components better suited for producing fuels, chemicals, and other products. This is generally because each of the lignin, cellulose and hemicellulose components demand distinct processing conditions, such as temperature, pressure, catalysts, reaction time, etc. in order to effectively break apart its polymer structure.

A need exists for a method for converting biomass to oxygenated compounds suitable for bioreforming processes, such as Aqueous-Phase Reforming (APR) and hydrodeoxygenation (HDO). Ideally, the method would convert biomass to carbohydrates, such as starches, saccharides, sugars and sugar alcohols, which are desirable feedstock for bioreforming processes.

Existing methods for converting biomass to usable feedstock are not sufficient to meet the growing needs of bioreforming processes. Hot water extraction of hemicelluloses from biomass has been well documented, but the sugars produced by hot water extraction are unstable at high temperatures leading to undesirable decomposition products. Therefore, the temperature of the water used for hot water extraction is limited, which can reduce the effectiveness of the hot water extraction.

Additionally, studies have shown that it is possible to convert microcrystalline cellulose (MCC) to polyols using hot, compressed water and a hydrogenation catalyst (Fukuoka & Dhepe, 2006; Luo et al., 2007; and Yan et al., 2006). Typical hydrogenation catalysts include ruthenium or platinum supported on carbon or aluminum oxide. However, these studies also show that only low levels of MCC are converted with these catalysts. Selectivity toward desired sugar alcohols is also low. Therefore, a process for converting biomass to polyols for further processing to fuels, chemicals, and other products would be beneficial.

APR and HDO are catalytic reforming processes that generate hydrogen and hydrocarbons from oxygenated compounds derived from a wide array of biomass. The oxygenated hydrocarbons include starches, mono- and poly-saccharides, sugars, sugar alcohols, etc. Various APR methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867 and 7,989,664 and U.S. Application Ser. No. 2011/0306804 (all to Cortright, and entitled "Methods and Systems for Generating Polyols"). Various APR and HDO methods and techniques are described in U.S. Patent Application Ser. Nos. 2008/0216391; 2008/0300434; and 2008/0300435 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

Biomass must be deconstructed to less complex oxygenated compounds prior to use as feedstock for bioreforming processes. There remains a need for cost-effective methods for separating biomass into streams suitable for use in APR, HDO and other bioreforming processes.

SUMMARY

The invention provides methods for converting a biomass slurry to lower molecular weight oxygenated hydrocarbons. The method generally involves catalytically reacting a biomass slurry comprising water and a biomass component with hydrogen and a heterogeneous deconstruction catalyst at a deconstruction temperature and a deconstruction pressure to produce an oxygenated hydrocarbon having a lower molecular weight than the biomass component.

One aspect of the invention is the composition of the biomass slurry. In one embodiment, the biomass component may be cellulose, lignocelluloses, agricultural residues, wood materials, energy crops, municipal solid waste, recycled fibers, corn stover, straw, bagasse, switch grass, miscanthus, sorghum, and poplar.

The heterogeneous deconstruction catalyst is capable of deconstructing biomass to form oxygenated hydrocarbons and/or oxygenates. In one embodiment, the heterogeneous deconstruction catalyst includes an acidic resin or a basic resin. The heterogeneous deconstruction catalyst may also include a support and a member selected from the group consisting of Cu, Fe, Ru, Ir, Co, Rh, Pt, Pd, Ni, W, Mo, alloys thereof, and combinations thereof. The heterogeneous deconstruction catalyst may include these elements alone or combined with one or more Cu, Mn, Cr, Mo, B, W, V, Nb, Ta, Ti, Zr, Y, La, Sc, Zn, Cd, Ag, Au, Sn, Ge, P, Al, Ga, In, Tl, Ce, and combinations thereof. In one embodiment, the deconstruction catalyst includes Ni, Ru, Ir, Pt, Pd, Rh, Co, or Mo and at least one member selected from W, B, Pt, Sn, Ag, Au, Rh, Co, and Mo.

The oxygenated hydrocarbons may include a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, a polyol, a diol, or a mono-oxygenate.

Another aspect of the invention is a method of converting a biomass slurry to lower weight oxygenated hydrocarbons and/or oxygenates. The method generally involves: (1) extracting the biomass slurry using hot water to produce a first liquid portion and a first solid slurry portion; (2) separating the first liquid portion from the first solid slurry portion; (3) catalytically reacting the first solid slurry portion with hydrogen in the presence of a heterogeneous deconstruction catalyst at a deconstruction temperature and a deconstruction pressure to produce a second solid slurry portion and a second liquid portion; (4) separating the second liquid portion from the second solid slurry portion; and (5) obtaining lower weight oxygenated hydrocarbons comprising a $C_{2+}O_{1+}$ hydrocarbon in a liquid phase from the first and second liquid portion.

The biomass slurry may include a cellulose, lignocellulose, agricultural residue, wood material, energy crop, municipal solid waste, recycled fiber, corn stover, straw, bagasse, switch grass, miscanthus, sorghum, and poplar. The first liquid portion may include a saccharide and an extractive, and the first solid slurry portion may include cellulose, hemicellulose, lignin, and ash.

The heterogeneous deconstruction catalyst includes an acidic resin or a basic resin and may include a support and a member adhered to the support selected from the group consisting of Cu, Fe, Ru, Ir, Co, Rh, Pt, Pd, Ni, W, Mo, alloys thereof, and combinations thereof.

The deconstruction reaction is conducted at a temperature and pressure suitable for deconstructing biomass. In one embodiment, the deconstruction temperature is in the range of about 80° C. to 350° C. and the deconstruction pressure is in the range of about 150 psi to 2000 psi.

The $C_{2+}O_{1+}$ oxygenated hydrocarbons may include a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, a polyol, a diol, or a mono-oxygenated hydrocarbon.

Another aspect of the invention is a method of converting cellulosic slurry to water-soluble oxygenated hydrocarbons. The method generally includes: (1) extracting the cellulosic slurry using an organosolv process to produce a first liquid portion and a first solid slurry portion; (2) separating the first liquid portion from the first solid slurry portion; (3) separating a solvent from the first liquid portion; (4) catalytically reacting the first solid slurry portion with hydrogen in the presence of a heterogeneous deconstruction catalyst at a deconstruction temperature and a deconstruction pressure to produce a second solid portion and a second liquid portion; (5) separating the second liquid portion from the second solid portion; and (6) obtaining water-soluble oxygenated hydrocarbons comprising a $C_{2+}O_{1+}$ hydrocarbon in an aqueous liquid phase from the first and second liquid portions.

In one embodiment, the method further includes recycling the solvent back into the organosolv process.

The biomass slurry may include a cellulose, lignocellulose, agricultural residue, wood material, energy crop, municipal solid waste, recycled fiber, corn stover, straw, bagasse, switch grass, miscanthus, sorghum, and poplar. The first liquid portion may include saccharides extractive, and lignen, and the first solid slurry portion may include cellulose, hemicellulose, lignin, and ash.

The heterogeneous deconstruction catalyst includes an acidic resin or a basic resin and may include a support and a member selected from the group consisting of Cu, Fe, Ru, Ir, Co, Rh, Pt, Pd, Ni, W, Mo, alloys thereof, and combinations thereof.

The deconstruction reaction is conducted at a temperature and pressure suitable for deconstructing biomass. In one embodiment, the deconstruction temperature is in the range of about 80° C. to 350° C. and the deconstruction pressure is in the range of about 100 psi to 2000 psi.

The $C_{2+}O_{1+}$ oxygenated hydrocarbons may include a starch, a carbohydrate, a polysaccharide, a disaccharide, a monosaccharide, a sugar, a sugar alcohol, an alditol, an organic acid, a phenol, a cresol, ethanediol, ethanedione, acetic acid, propanol, propanediol, propionic acid, glycerol, glyceraldehyde, dihydroxyacetone, lactic acid, pyruvic acid, malonic acid, a butanediol, butanoic acid, an aldotetrose, tartaric acid, an aldopentose, an aldohexose, a ketotetrose, a ketopentose, a ketohexose, a hemicellulose, a cellulosic derivative, a lignocellulosic derivative, and a polyol, a diol, or a mono-oxygenated hydrocarbon.

DESCRIPTION OF THE DRAWINGS

FIG. 2 is a chart illustrating the conversion of 10% cellulose to polyols at 260° C. using an Ru—C catalyst and a short soak time.

FIG. 3 is a chart illustrating the product yield in aqueous fraction from MCC at 260° C. using a Ru—C catalyst and a short soak time.

FIG. 4 is a chart illustrating difference in conversion of 10% cellulose to polyols at 260° C. using a Ru—C catalyst for a short soak time and a longer soak time.

FIG. 5 is a chart illustrating the difference in product yield in aqueous fraction from MCC at 260° C. using a Ru—C catalyst for a short soak time and a longer soak time.

FIG. 6 is a chart illustrating the conversion of 10% cellulose to polyols at 260° C. using various hydrogenolysis catalysts.

FIG. 7 is a chart illustrating product yields resulting from using various hydrogenolysis catalysts.

FIG. 8 is a chart illustrating the difference between bagasse and MCC conversion using an Ru—C catalyst.

FIG. 9 is a chart illustrating the difference in product yields between bagasse and MCC conversion using a Ru—C catalyst.

FIG. 10 is a chart illustrating the conversion of 10% bagasse to polyols using phosphoric acid, PSA and Amberlyst 70.

FIG. 11 is a chart illustrating the product yields from the conversion of 10% bagasse to polyols using phosphoric acid, PSA and Amberlyst 70.

FIG. 12 is a chart illustrating the results from the conversion of bagasse at different particle sizes.

FIG. 13 is a chart illustrating the products yields from the conversion of bagasse at different particle sizes.

FIG. 14 is a chart illustrating the results from the conversion of 10% microcrystalline cellulose using various catalysts at 260° C.

FIG. 15 is a chart illustrating the product yields from the conversion of 10% microcrystalline cellulose using various catalysts at 260° C.

FIG. 16 is a chart illustrating the results from the conversion of corn fiber using various catalysts at variable temperatures.

FIG. 17 is a chart illustrating the product yields from the conversion of corn fiber using various catalysts at variable temperatures.

FIG. 18 is a chart illustrating the results from the conversion of various biomass slurries using various catalysts at 260° C.

FIG. 19 is a chart illustrating the product yields from the conversion of various biomass slurries using various catalysts at 260° C.

FIG. 20 is a chart illustrating the results from the conversion of 10% bagasse using various catalysts at 300° C.

FIG. 21 is a chart illustrating the oxygenated product yields from the conversion of 10% bagasse using various catalysts at 300° C.

FIG. 22 is a chart illustrating the product yields from the conversion of 10% bagasse using various catalysts at 300° C.

FIG. 23 is a chart illustrating the results from the conversion of various biomass slurries using a nickel tungsten carbide catalyst.

FIG. 24 is a chart illustrating the product yields from the conversion of various biomass slurries using a nickel tungsten carbide catalyst.

FIG. 26 is a chart illustrating the results from the conversion of various biomass slurries using a variety of catalysts.

FIG. 27 is a chart illustrating the deoxygenation level of various biomass slurries using a variety of catalysts.

FIG. 28 is a chart illustrating the product yields from the conversion of various biomass slurries using a variety of catalysts.

FIG. 29 is a chart illustrating the results from the conversion of various biomass slurries using a variety of catalysts and the amount of carbon converted to the aqueous phase.

FIGS. 30A and 30B are charts illustrating the carbon conversion to the aqueous phase at varying reaction hydrogen partial pressures with microcrystalline cellulose.

FIG. 31 is a chart illustrating product selectivity at varying reaction hydrogen partial pressures with microcrystalline cellulose.

FIG. 32 is a chart illustrating the degree of oxygenation at varying reaction hydrogen partial pressures with microcrystalline cellulose.

FIGS. 33A and 33B are charts illustrating the overall balances and biomass conversion results of loblolly pine deconstruction at varying temperatures and pressures.

DETAILED DESCRIPTION OF THE INVENTION

The present invention relates to methods, reactor systems, and catalysts for converting biomass to less complex oxygenated hydrocarbons for use in downstream bioreforming processes to produce biofuels and chemicals. The invention includes methods of converting biomass to lignin and lignocellulosic derivatives, cellulose and cellulosic derivatives, hemicellulose and hemicellulosic derivatives, carbohydrates, starches, polysaccharides, disaccharides, monosaccharides, sugars, sugar alcohols, alditols, polyols, diols, mono-oxygenated hydrocarbons, and mixtures thereof, using hydrogen and a heterogeneous catalyst.

As used herein, the term "biomass" refers to, without limitation, organic materials produced by plants (such as leaves, roots, seeds and stalks), and microbial and animal metabolic wastes. Common biomass sources include: (1) agricultural residues, including corn stover, straw, seed hulls, sugarcane leavings, bagasse, nutshells, cotton gin trash, and manure from cattle, poultry, and hogs; (2) wood materials, including wood or bark, sawdust, timber slash, and mill scrap; (3) municipal solid waste, including recycled fiber, waste paper and yard clippings; and (4) energy crops, including poplars, willows, switch grass, miscanthus, sorghum, alfalfa, prairie bluestream, corn, soybean, and the like. The term also refers to the primary building blocks of the above, namely, lignin, cellulose, hemicellulose and carbohydrates, such as saccharides, sugars and starches, among others.

As used herein, the term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, diols and other polyols, using aqueous phase reforming, hydrogenation, hydrogenolyis, hydrodeoxygenation and/or other conversion processes involving the use of heterogeneous catalysts. Bioreforming also includes the further catalytic conversion of such lower molecular weight oxygenated compounds to $C_{4+}$ compounds.

Figure 1:
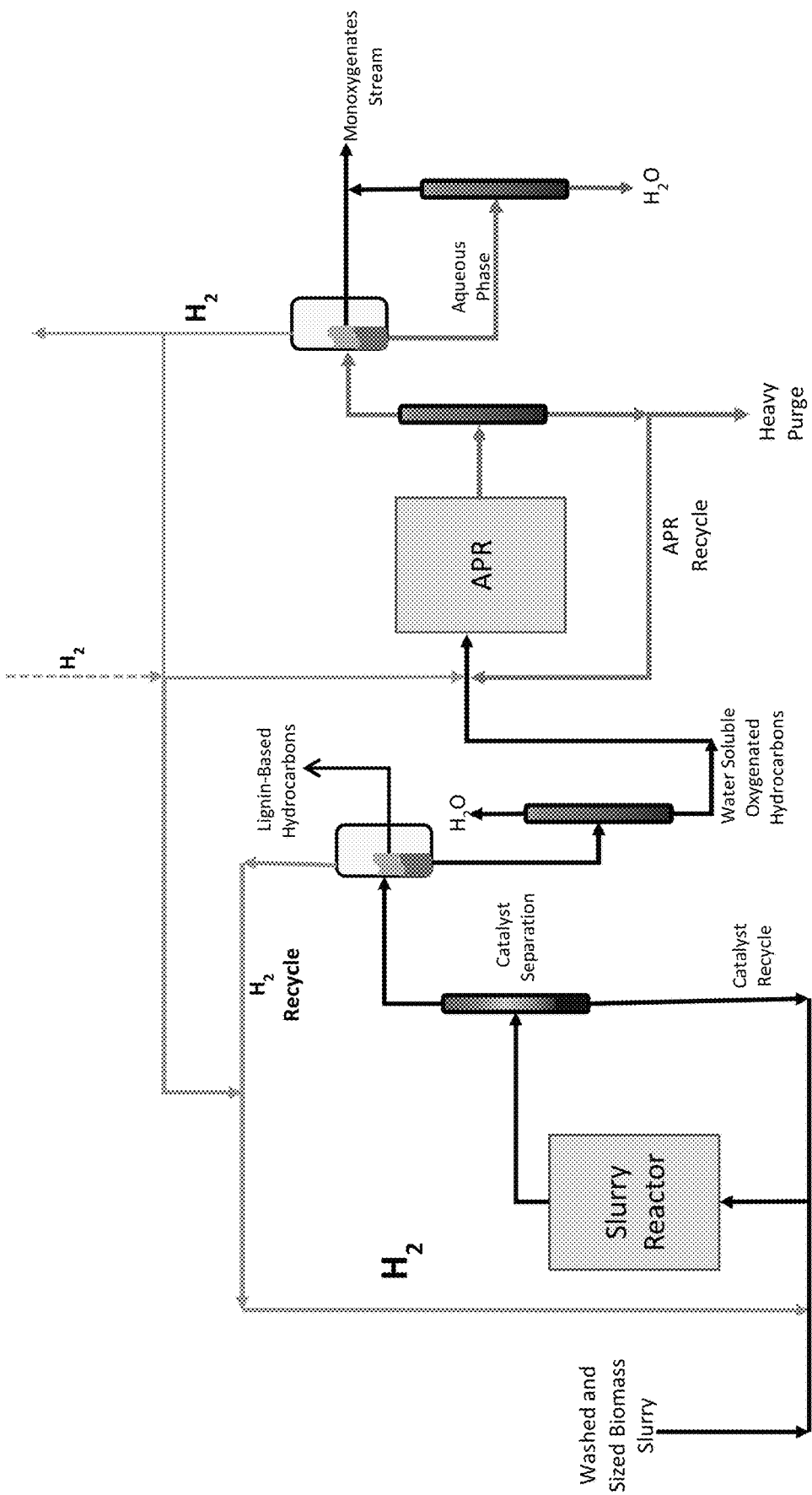
FIG. 1 is a flow diagram illustrating one embodiment of the present invention.

In the present invention, biomass is converted to a biomass hydrolyzate using hydrogen and a heterogeneous deconstruction catalyst. The general process is illustrated in FIG. 1. A biomass slurry is created by combining biomass that has been chopped, shredded, pressed, ground or processed to a size amenable for conversion, with water and/or a solvent. The biomass slurry is then passed into a reactor where it reacts with hydrogen and a deconstruction catalyst at a deconstruction temperature and a deconstruction pressure to produce oxygenated hydrocarbons that can be used in downstream bioreforming processes or converted directly to $C_{4+}$ hydrocarbons, such as $C_{4+}$ alkanes, $C_{4+}$ alkenes, and aromatic compounds.

Figure 25:
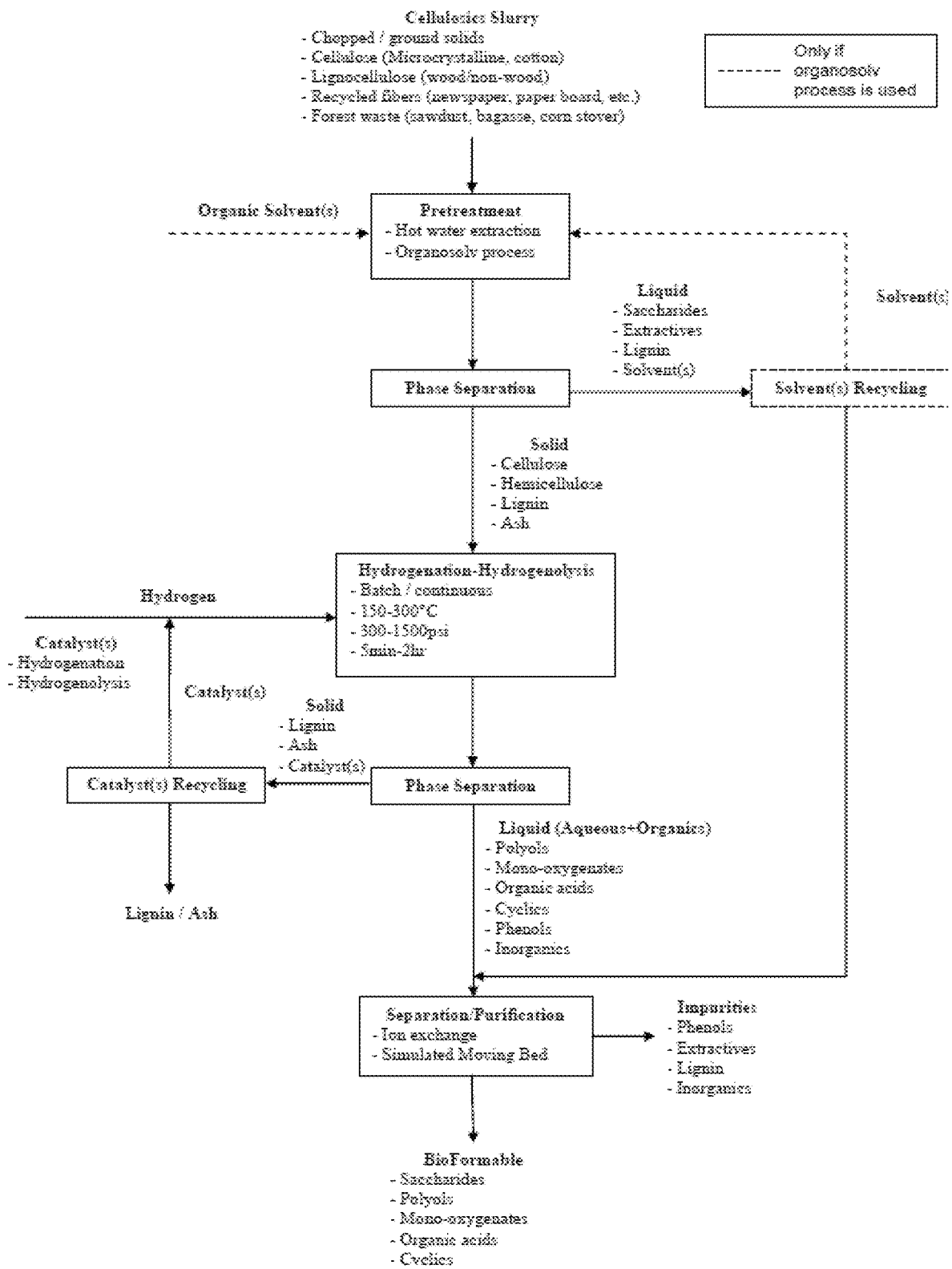
FIG. 25 is a flow diagram illustrating one embodiment of the present invention employing a hot water extraction or a solvent pretreatment step.

In one embodiment, illustrated in FIG. 25, the present invention may also include an initial pretreatment hot water or solvent-based extraction step. The hot water extraction or solvent based process produces a liquid phase slurry and a solid phase slurry. The liquid phase includes hemicellulose, lignin, saccharides and extractives. If a solvent-based process is used, the liquid phase also includes solvent, which can be separated from the liquid phase and recycled for re-use. The solid phase slurry includes the remaining cellulose, hemicellulose, lignin, and ash. In this embodiment, the process generally involves: (1) extracting the biomass slurry using hot water or the solvent to produce a first liquid portion and a first solid slurry portion; (2) separating the first liquid portion from the first solid slurry portion; (3) catalytically reacting the first solid slurry portion with hydrogen in the presence of a heterogeneous deconstruction catalyst at a deconstruction temperature and a deconstruction pressure to produce a second solid slurry portion and a second liquid portion; (4) separating the second liquid portion from the second solid slurry portion; and (5) obtaining from the first and second liquid portion, lower weight oxygenated hydrocarbons (e.g., $C_{2+}O_{1+}$ oxygenated hydrocarbons). If a solvent is used, the liquid phase can be separated from the solid phase slurry to recover the solvent using known separation procedures.

Solvent-based applications are well known in the art. Organosolv processes use organic solvents such as ionic liquids, acetone, ethanol, 4-methyl-2-pentanone, and solvent mixtures, to fractionate lignocellulosic biomass into cellulose, hemicellulose, and lignin streams (Paszner 1984; Muurinen 2000; and Bozell 1998). Strong-acid processes use concentrated hydrochloric acid, phosphoric acid, sulfuric acid or other strong organic acids as the depolymerization agent, while weak acid processes involve the use of dilute strong acids, acetic acid, oxalic acid, hydrofluoric acid, or other weak acids as the solvent. Enzymatic processes have also recently gained prominence and include the use of enzymes as a biocatalyst to decrystalize the structure of the biomass and allow further hydrolysis to useable feedstocks.

If a solvent is used, once the solvent is recovered, the resulting liquid phase slurry (absent a significant portion of the solvent) can be recycled into the biomass slurry, recombined with the solid phase slurry, used in a bioreforming process or, alternatively, used as a feedstock for other conversion processes, including the production of fuels and chemicals using fermentation or enzymatic technologies.

The biomass slurry, solid phase slurry or combined liquid/solid phase slurry is reacted with hydrogen over a deconstruction catalyst under conditions of temperature and pressure effective to cause a reaction that converts a portion of the lignin, cellulose and hemicellulose to a biomass product stream that includes less complex oxygenated compounds, extractives and other inorganic products. The oxygenated compounds—referred to as the biomass hydrolyzate—will generally include carbohydrates, starches, polysaccharides, disaccharides, monosaccharides, sugars, sugar alcohols, alditols, monooxygenates, organic acids, phenols, and cresols. Preferably, the biomass hydrolyzate includes sugar, sugar alcohols, starch, saccharides and other polyhydric alcohols. More preferably, the biomass hydrolyzate includes a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, arabitol, or glycol. In certain embodiments, the biomass hydrolyzate may also include alcohols, ketones, cyclic ethers, esters, carboxylic acids, aldehydes, diols and other polyols that may be useful as an organosolv-like solvent. In other embodiments, the biomass hydrolyzate may also include mono-oxygenated hydrocarbons that may be further converted to $C_{4+}$ hydrocarbons, such as $C_{4+}$ alkanes, $C_{4+}$ alkenes, and aromatic compounds, including benzene, toluene, xylene, which are useful as liquid fuels and chemicals. Extractives will typically include ash, terpenoids, stilbenes, flavonoids, proteins, etc. The product stream may also include unreacted or under-reacted biomass.

The resulting biomass hydrolyzate may be collected for further processing in a bioreforming process or, alternatively, used as a feedstock for other conversion processes, including the production of fuels and chemicals using fermentation or enzymatic technologies. For example, water-soluble carbohydrates, such as starch, monosaccharides, disaccharides, polysaccharides, sugars, and sugar alcohols, and water-soluble derivatives from the lignin, hemicellulose and cellulose are suitable for use in bioreforming processes. Alternatively, the resulting biomass hydrolyzate may be recycled and combined in the biomass slurry for further conversion.

In certain applications, the biomass product stream undergoes one or more separation steps to separate the extractives, unreacted biomass and under-reacted biomass from the product stream to provide the biomass hydrolyzate. The biomass hydrolyzate may also require further processing to separate aqueous phase products from organic phase products, such as lignin-based hydrocarbons that are not suitable for further conversion. The biomass hydrolyzate may also be dewatered or further purified prior to being introduced into further processing steps. Such dewatering and purification processes are known in the art and can include simulated moving bed technology, distillation, filtration, etc.

The deconstruction catalyst is a heterogeneous catalyst having one or more materials capable of catalyzing a reaction between hydrogen and lignin, cellulose, hemicellulose and their derivatives to produce the desired oxygenated compounds. The heterogeneous deconstruction catalyst may include, without limitation, acid modified resin, base modified resin, and/or one or more of Cu, Fe, Ru, Ir, Co, Rh, Pt, Pd, Ni, W, Mo, alloys and combinations thereof. The deconstruction catalyst may include these elements alone or combined with one or more Cu, Mn, Cr, Mo, B, W, V, Nb, Ta, Ti, Zr, Y, La, Sc, Zn, Cd, Ag, Au, Sn, Ge, P, Al, Ga, In, Tl, Ce, and combinations thereof. In one embodiment, the deconstruction catalyst includes Ni, Ru, Ir, Pt, Pd, Rh, Co, or Mo and at least one member selected from W, B, Pt, Sn, Ag, Au, Rh, Co, and Mo.

Resins will generally include basic or acidic supports (e.g., supports having low isoelectric points) that are able to catalyze deconstruction reactions of biomass, followed by hydrogenation reactions in the presence of $H_2$, leading to carbon atoms that are not bonded to oxygen atoms. Heteropolyacids are a class of solid-phase acids exemplified by such species as $H_{3+x}PMO_{12-x}V_xO_{40}$, $H_4SiW_{12}O_{40}$, $H_3PW_{12}O_{40}$, and $H_6P2W_{18}O_{62}$. Heteropolyacids also have a well-defined local structure, the most common of which is the tungsten-based Keggin structure. Basic resins include resins that exhibit basic functionality, such as Amberlyst.

The deconstruction catalyst is either self-supporting or includes a supporting material. The support may contain any one or more of nitride, carbon, silica, alumina, zirconia, titania, tungsten, vanadia, ceria, zinc oxide, chromia, boron nitride, tungstated zirconia, heteropolyacids, kieselguhr, hydroxyapatite, and mixtures thereof. Preferable supports are carbon, m-$ZrO_2$, and W—$ZrO_2$. In one embodiment, the deconstruction catalyst includes Ni:Mo, Pd:Mo, Rh:Mo, Co:Mo, Pd:Ru, Pt:Re, or PtRh on a m-$ZrO_2$ support. In another embodiment, the deconstruction catalyst includes Ru, Ru:Pt, Pd:Ru, Pt:Re, Pt:Rh, Pd:Mo, Pd:Ag, or Ru:Pt:Sn on a carbon or W—$ZrO_2$ support. In yet another embodiment the deconstruction catalyst includes Fe, Co, Ni, Cu, Ru, Rh, Pd, Pt, Re, Mo, or W on a carbon support. The support may also serve as a functional catalyst, such as in the case of acidic or basic resins or supports having acidic or basic functionality.

In one embodiment, the deconstruction catalyst is formed in a honeycombed monolith design such that the biomass slurry, solid phase slurry or the solid/liquid phase slurry can flow through the deconstruction catalyst. In another embodiment, the deconstruction catalyst includes a magnetic element such as Fe or Co such that the deconstruction catalyst can be easily separated from the resulting product mixture.

The biomass slurry, solid phase slurry or the solid/liquid phase slurry is reacted with hydrogen over the deconstruction catalyst under conditions of temperature and pressure effective to convert cellulose and hemicellulose to polyols, monooxygenates, organic acids, cyclic, phenols, and inorganics. The specific products produced will depend on various factors, including the composition of the slurry, reaction temperature, reaction pressure, water concentration, hydrogen concentration, the reactivity of the catalyst, and the flow rate of the slurry as it affects the space velocity (the mass/volume of reactant per unit of catalyst per unit of time), gas hourly space velocity (GHSV), and weight hourly space velocity.

The deconstruction process can be either batch or continuous. In one embodiment, the deconstruction process is a continuous process using one or more continuous stirred-tank reactors in parallel or in series. The deconstruction temperature will generally be greater than 80° C., or 120° C. or 150° C., or 180° C., or 200° C., or 250° C., and less than 350° C., or 325° C., or 300° C., or 280° C., or 260° C. In one embodiment, the deconstruction temperature is between about 80° C. and 350° C., or between about 150° C. and 350° C., or between about 150° C. and 300° C., or between about 200° C. and 260° C., or between about 250° C. and 300° C. The deconstruction pressure is generally greater than 100 psi, or 250 psi, or 300 psi, or 625 psi, or 900 psi, or 1000 psi, or 1200 psi, and less than 2000 psi, or 1500 psi, or 1200 psi. In one embodiment, the deconstruction temperature is between about 100 psi and 2000 psi, or between about 300 psi and 1500 psi, or between about 1000 psi and 1500 psi. Preferably, the slurry contacts the deconstruction catalyst for between approximately 5 minutes and 2 hours.

In general, the reaction should be conducted under conditions where the residence time of the slurry over the catalyst is appropriate to generate the desired products. For example, the WHSV for the reaction may be at least about 0.1 gram of biomass per gram of catalyst per hour, and more preferably the WHSV is about 0.1 to 40.0 g/g hr, including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.83, 0.85, 0.85, 1.71, 1.72, 1.73, etc.).

The present invention is able to effectively convert the biomass components to lower molecular weight oxygenated hydrocarbons due to the presence of hydrogen in the system. The hydrogen facilitates the reaction and conversion process by immediately reacting with the various reaction intermediates and the deconstruction catalyst to produce products that are more stable and less subject to degradation. The hydrogen may be generated in situ using aqueous phase reforming (in situ generated $H_2$ or APR $H_2$), whether in the biomass deconstruction reactor or in downstream processes using the biomass hydrolyzate as a feedstock, or a combination of APR $H_2$, external $H_2$ or recycled $H_2$, or just simply external $H_2$ or recycled $H_2$. The term "external $H_2$" refers to hydrogen that does not originate from the biomass solution, but is added to the reactor system from an external source. The term "recycled $H_2$" refers to unconsumed hydrogen which is collected and then recycled back into the reactor system for further use. External $H_2$ and recycled $H_2$ may also be referred to collectively or individually as "supplemental $H_2$." In general, the amount of $H_2$ added should maintain the reaction pressure within the system at the desired levels, or increase the molar ratio of hydrogen to carbon and/or oxygen in order to enhance the production yield of certain reaction product types.

The deconstruction process may also include the introduction of supplemental materials to the slurry to assist with the biomass deconstruction or the further conversion of the oxygenated compounds to products more suited for bioreforming processes. Supplemental materials may include dopants, such as acetone, gluconic acid, acetic acid, $H_2SO_4$ and $H_3PO_4$.

The deconstruction process converts the lignin, cellulose and hemicellulose in the liquid and solid phase to an organic complex including carbohydrates, starches, polysaccharides, disaccharides, monosaccharides, sugars, sugar alcohols, alditols, mono-oxygenates, organic acids, phenols, and cresols. In certain applications, the biomass product stream undergoes one or more separation steps to separate the catalyst (if any), extractives and unreacted biomass from the biomass hydrolyzate. The biomass hydrolyzate may also require further processing to separate aqueous phase products from organic phase products, such as lignin-based hydrocarbons not suitable for bioreforming processes. The biomass hydrolyzate may also be dewatered or further purified prior to being introduced into the bioreforming process. Such dewatering and purification processes are known in the art and can include simulated moving bed technology, distillation, filtration, etc.

After separating the impurities, the product stream, suitable for use in bioreforming processes, includes oxygenated hydrocarbons. Oxygenated hydrocarbons may be any water-soluble oxygenated hydrocarbon having two or more carbon atoms and at least one oxygen atom (referred to herein as $C_{2+}O_{1+}$ hydrocarbons). Preferably, the oxygenated hydrocarbon has 2 to 12 carbon atoms ($C_{2-12}O_{1-11}$ hydrocarbon), and more preferably 2 to 6 carbon atoms ($C_{2-6}O_{1-6}$ hydrocarbon), and 1, 2, 3, 4, 5, 6, or more oxygen atoms. The oxygenated hydrocarbon may also have an oxygen-to-carbon ratio ranging from 0.5:1 to 1.5:1, including ratios of 0.75:1.0, 1.0:1.0, 1.25:1.0, 1.5:1.0, and other ratios between. In one example, the oxygenated hydrocarbon has an oxygen-to-carbon ratio of 1:1. Nonlimiting examples of preferred water-soluble oxygenated hydrocarbons include starches, carbohydrates, polysaccharides, disaccharides, monosaccharides, sugars, sugar alcohols, alditols, organic acids, phenols, cresols, ethanediol, ethanedione, acetic acid, propanol, propanediol, propionic acid, glycerol, glyceraldehyde, dihydroxyacetone, lactic acid, pyruvic acid, malonic acid, butanediols, butanoic acid, aldotetroses, tartaric acid, aldopentoses, aldohexoses, ketotetroses, ketopentoses, ketohexoses, hemicelluloses, cellulosic derivatives, lignocellulosic derivatives, polyols and the like. Preferably, the oxygenated hydrocarbon includes starches, sugar, sugar alcohols, saccharides and other polyhydric alcohols. More preferably, the oxygenated hydrocarbon is a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, ribitol, or glycol.

The product stream may also include smaller oxygenates, such as alcohols, ketones, cyclic ethers, esters, carboxylic acids, aldehydes, diols and other polyols, that may be further converted to $C_{4+}$ hydrocarbons, such as $C_{4+}$ alkanes, $C_{4+}$ alkenes, and aromatic compounds, including benzene, toluene, xylene, using a bioreforming process. As used herein, "oxygenates" generically refers to hydrocarbon compounds having 2 or more carbon atoms and 1, 2 or 3 oxygen atoms (referred to herein as $C_{2+}O_{1-3}$ hydrocarbons), such as alcohols, ketones, aldehydes, furans, hydroxy carboxylic acids, carboxylic acids, diols and triols. Preferably, the oxygenates have from 2 to 6 carbon atoms, or 3 to 6 carbon atoms. Alcohols may include, without limitation, primary, secondary, linear, branched or cyclic $C_{2+}$ alcohols, such as ethanol, n-propyl alcohol, isopropyl alcohol, butyl alcohol, isobutyl alcohol, butanol, pentanol, cyclopentanol, hexanol, cyclohexanol, 2-methyl-cyclopentanonol, heptanol, octanol, nonanol, decanol, undecanol, dodecanol, and isomers thereof. The ketones may include, without limitation, hydroxyketones, cyclic ketones, diketones, acetone, propanone, 2-oxopropanal, butanone, butane-2,3-dione, 3-hydroxybutan-2-one, pentanone, cyclopentanone, pentane-2,3-dione, pentane-2,4-dione, hexanone, cyclohexanone, 2-methyl-cyclopentanone, heptanone, octanone, nonanone, decanone, undecanone, dodecanone, methylglyoxal, butanedione, pentanedione, diketohexane, and isomers thereof. The aldehydes may include, without limitation, hydroxyaldehydes, acetaldehyde, propionaldehyde, butyraldehyde, pentanal, hexanal, heptanal, octanal, nonal, decanal, undecanal, dodecanal, and isomers thereof. The carboxylic acids may include, without limitation, formic acid, acetic acid, propionic acid, butanoic acid, pentanoic acid, hexanoic acid, heptanoic acid, isomers and derivatives thereof, including hydroxylated derivatives, such as 2-hydroxybutanoic acid and lactic acid. The diols may include, without limitation, ethylene glycol, propylene glycol, 1,3-propanediol, butanediol, pentanediol, hexanediol, heptanediol, octanediol, nonanediol, decanediol, undecanediol, dodecanediol, and isomers thereof. The triols may include, without limitation, glycerol, 1,1,1 tris(hydroxymethyl)-ethane (trimethylolethane), trimethylolpropane, hexanetriol, and isomers thereof. Furans and furfurals include, without limitation, furan, tetrahydrofuran, dihydrofuran, 2-furan methanol, 2-methyl-tetrahydrofuran, 2,5-dimethyl-tetrahydrofuran, 2-methyl furan, 2-ethyl-tetrahydrofuran, 2-ethyl furan, hydroxylmethylfurfural, 3-hydroxytetrahydrofuran, tetrahydro-3-furanol, 2,5-dimethyl furan, 5-hydroxymethyl-2 (5H)-furanone, dihydro-5-(hydroxymethyl)-2(3H)-furanone, tetrahydro-2-furoic acid, dihydro-5-(hydroxymethyl)-2(3H)-furanone, tetrahydrofurfuryl alcohol, 1-(2-furyl) ethanol, hydroxymethyltetrahydrofurfural, and isomers thereof.

As for the unreacted solids, the deconstruction catalyst can be recycled for re-use in upstream processes. The lignin, ash and other extractives can be purged from the system and used in other processes. For example, the lignin can be burned to provide process heat, while the proteinaceous material can be used for animal feed or as other products.

Example 1

A biomass slurry containing 10 wt % microcrystalline cellulose (MCC) in water was prepared and converted to a biomass hydrolyzate using ruthenium on a carbon support. Experiments were conducted in a Parr reactor at 240° C. and 260° C., and at variable processing times of 10 and 20 minutes.

It was discovered that the thermal decomposition of the sugar intermediates is minimized/avoided with the formation of the more stable oxygenates that arise from the hydrogenolysis of the saccharides and polysaccharides. The Ru—C catalyst and short soak times at 260° C. provided high conversion and sugar-polyol yields, with 72% conversion of microcrystalline cellulose (MCC) and a sugars-polyol yield of 48%. A high yield of sorbitol (27 g/g MCC) was found with Ru/C catalyst as illustrated in FIGS. 2 and 3. The mass balance was 94% and aqueous analytical balance was 72%.

The effectiveness of the longer reaction time (20 min vs. 10 min) is shown in FIGS. 4 and 5. The extended reaction enhanced both the conversion and hydrogenolysis of the MCC.

Example 2

Several deconstruction catalysts were analyzed for their ability to convert 10% MCC in water to sugars/polyols. Experiments were conducted in a Parr reactor at 260° C. for 10 minutes. As illustrated in FIGS. 6 and 7, platinum improves cellulose conversion and provokes higher extent hydrogenolysis.

Example 3

A biomass slurry containing 10 wt % bagasse was converted to biomass hydrolyzate using the Ru/C catalyst as described in Example 1. Experiments were conducted in a Parr reactor at 245° C. and 260° C. for 10 minutes. FIGS. 8 and 9 provide a comparison of the conversion and product yields for bagasse versus the MCC of Example 1.

Example 4

Acidic resins containing a sulfonate group were investigated for their ability to hydrolyze bagasse using the catalytic depolymerization techniques of the present invention. Soluble polystyrene sulfonic acid (PSA) and phosphoric acid were used as hydrolyzing acids for comparison. Ruthenium supported on carbon was used as a hydrogenation catalyst. The detailed experimental conditions are listed in Table 1.

TABLE 1

Study of acidity of acidic resin's functional group

| Trial | Bagasse (wt %) | Acid | Temp (° C.) | Time* (min) | $H_2$ Pressure (psi) | Hydrogenation Catalyst** |
|---|---|---|---|---|---|---|
| 1 | 10 | 5% H3PO4 | 190 | 90 | 500 | 1% Ru/C |
| 2 | 10 | 5% PSA | 190 | 90 | 500 | 1% Ru/C |
| 3 | 10 | 1% PSA | 190 | 90 | 500 | 1% Ru/C |
| 4 | 10 | 0.25:1 Amberlyst 70:Bagasse | 190 | 90 | 500 | 1% Ru/C |

*Total time includes 30 minutes of heating
Catalyst load is 0.3:1 catalyst:bagasse The results of bagasse hydrolysis using phosphoric acid, PSA and Amberlyst 70 are compared in FIGS. 10 and 11**. Using 5% PSA (Trial 2) achieved similar bagasse hydrolysis results as using 5% $H_3PO_4$ (Trial 1), converting ~40% bagasse into sugars, polyols, organic acids, and a substantial amount of other decomposition products. 1% PSA (Trial 3) converted less bagasse than 5% homogeneous acids. The 1%

PSA yielded a higher net sugar/polyol yield because the 5% PSA caused more severe sugar degradation. The "soluble homogeneous" acid catalysts had larger yields of unknowns versus the solid acid catalyst, Amberlyst 70. This is consistent with insufficient hydrogenation of the resulting monomeric sugars to the more stable sugar alcohols that would presumably prevent sugar degradation. The reduced hydrogenation activity could be due to fouling of the hydrogenation catalyst with the soluble PSA, decomposition products of the sugar, or solubilized lignin. The Amberlyst 70 is a resin that has high temperature stability of 190° C., but the upper temperature range for the soluble PSA is probably significantly lower. The Amberlyst 70 remains intact as a heterogeneous solid acid and therefore does not poison or cause fouling of the hydrogenation catalyst. In the case of the 5% $H_3PO_4$, the hydrogen phosphate or impurities present in the phosphoric acid (S, Ca, N, etc.) might poison the hydrogenation catalyst.

When using the Amberlyst 70, xylitol is the major product and sorbitol, arabitol, and acetic acid are the minor products. These products result from depolymerization of hemicellulose which accounts for 25% of the sugarcane bagasse used in this study. The rest of the bagasse conversion (up to 40%) is primarily from solubilized extractives and lignin. This is consistent with the acid-catalyzed hydrolysis of hemicellulose, which involves solubilization, hydrogenation and partial deconstruction of the reducing sugars under these conditions. This is consistent with the two-stage acid hydrolysis processes in which the first stage uses dilute $H_2SO_4$ and has proven to be an efficient means of producing xylose from hemicellulose (Roberto 1994; Silva 1996).

When using the soluble homogeneous acids, glucose, oxalic acid and unknowns are the major components in the product mix. Xylose, xylitol, arabitol, acetic acid, and formic acid are present at lower levels. The results are consistent with the acid-catalyzed hydrolysis of both hemicellulose and cellulose when more drastic reaction conditions are employed. Glucose can be produced from cellulose hydrolysis and xylose decomposes rapidly, resulting in unidentified products. The product distribution is consistent with the acid-catalyzed hydrolysis of hemicellulose, its partial hydrogenation before the hydrogenation activity stopped, and decomposition to unknowns of the non-hydrogenated sugars. The acid hydrolysis of cellulose could have occurred in parallel or slightly delayed to the hemicellulose hydrolysis due to the increased difficulty to solubilize cellulose.

As a summary, soluble polystyrene sulfonic acid can convert 40% sugarcane bagasse at temperature of 190° C., producing sugars, polyols, organic acids and degradation products. The 12% sugar/polyol yield is similar to using 5% phosphoric acid. This indicates that polystyrene sulfonic acid has a high enough acidity to hydrolyze biomass analogous to a similar concentration of homogenous acid.

Example 5

Experiments were conducted to determine the impact of biomass particle size on homogeneous and heterogeneous hydrolysis. Ground sugarcane bagasse particles (<20, 40, 60 mesh, <840, 420, and 250 µm, respectively) were used as representing lignocellulosic material. Hot water extraction and hydrolysis using acidic resin (Amberlyst 70) were used as representative homogeneous and heterogeneous processes. The detailed experimental conditions are listed in Table 2.

The results of hydrolysis using different bagasse particle sizes are compared in FIGS. 12 and 13. Similar hydrolysis results were observed among different bagasse particle sizes. Finer particles facilitate bagasse conversion using heterogeneous catalyst, but not significantly. Using a solid acid catalyst enhances hemicellulose hydrolysis producing more xylose and glucose than the water-only extraction. No significant increase of glucose yield with decreasing bagasse particle size was achieved using acidic resin, indicating that grinding bagasse to the smaller particle sizes tested here does not expose more cellulose to solid acids.

TABLE 2

Hydrolysis of sugarcane bagasse using different bagasse particle sizes

| WC | Bagasse (wt %) | Acid | Temp* (° C.) | Time** (min) | Analytical Hydrolysis |
|---|---|---|---|---|---|
| 1 | 10 | — | 170 | 120 | 3% |
| 2 | 10 | — | 170 | 120 | $H_2SO_4$, |
| 3 | 10 | — | 170 | 120 | 120° C., 60 min |
| 4 | 10 | 0.25:1 Amberlyst 70 | 160 | 120 | — |
| 5 | 10 | 0.25:1 Amberlyst 70 | 160 | 120 | — |
| 6 | 10 | 0.25:1 Amberlyst 70 | 160 | 120 | — |

*Temperatures are determined by previous studies providing most sugar/polyol yield
**Total time includes 60 minutes of heating The results suggest that the mild reaction conditions used here, i.e., relatively low temperature and short reaction time, leads to limited bagasse conversion in all cases, and that the Amberlyst resin case did better than water extraction only. High DP oligosaccharides released from hemicellulose under high temperature are hydrolyzed with in-situ acid hydrolysis. However, these big molecular saccharides are not water-soluble after being cooled to room temperature. This explains the lower sugar yield by water only extraction with analytical hydrolysis.

Example 6

Four different deconstruction catalysts were investigated for the conversion of microcrystalline cellulose. Platinum and Ruthenium were selected as deconstruction catalysts. Activated carbon, tungstated zirconia, and α-alumina were selected as catalyst supports. Elevated temperature (260° C.) and $H_2$ pressure (600 psi $H_2$ initial reactor pressure), and short reaction time (60 min heating and 10 min retention) were applied to all experiments. The hydrogenolysis results are shown in FIGS. 14 and 15.

Platinum supported on alumina, among the tested four catalysts, gives the highest conversion of microcrystalline cellulose into desired products. Ruthenium supported on activated carbon demonstrated high microcrystalline cellulose conversion (~70%) and polyol products yield (50%). This result indicates that highly crystalline cellulose can be hydrolyzed at elevated temperature and pressure using deconstruction catalyst with inert support. Alumina support does not show major impacts on cellulose hydrolysis given that conversion drops significantly when supported catalytic metal is changed to ruthenium. When solid acid (tungstenated zirconia) is applied as catalyst support, undesired reactions (degradation and recondensation) lead to poor yield of polyols and production of unidentified compounds.

FIG. 15 shows that major products from the deconstruction of microcrystalline cellulose are polyols (from $C_2$ to $C_6$) and other oxygenates. Ruthenium shows high capacity of hydrogenation resulting in significant production of sorbitol. Platinum shows good hydrogenolysis performance including both deoxygenation and carbon-carbon bond cleavage.

In summary, highly efficient deconstruction of microcrystalline cellulose can be achieved using deconstruction catalysts under elevated temperature and pressure. Major products are polyols, organic acids, and oxygenates, etc., that can be utilized in the bioreforming process being developed by Virent, Inc. (Madison, Wis.).

Example 7

A 10 wt % corn fiber in water was hydrolyzed using various catalysts and processing conditions. Three reaction conditions were selected: (1) Amberlyst 70+Ru/C catalyst at 190° C. and 600 psi $H_2$, (2) Ru/C catalyst at 200° C. and 600 psi $H_2$, and (3) Ru/C catalyst at 260° C. and 600 psi $H_2$. The experimental results are shown in FIGS. 16 and 17.

It can be seen that using an acidic resin in this study, improves corn fiber conversion. But reduced hydrogenation catalyst activity can also be observed, especially under the elevated temperature. This poor hydrogenation performance is understood to be caused by impurities introduced by corn fiber hydrolysis, which can be lignin, protein, and sugar decomposition products.

Example 8

Biomass deconstruction of various biomass samples was explored using deconstruction catalysts containing ruthenium and ruthenium/rhodium on carbon. Reaction conditions were 260° C. and >1000 psi $H_2$. Results show that the catalysts are able to convert 60-100% MCC, soda hardwood (Kappa 110) pulp, and sugarcane bagasse. The major products are sugars/polyols and decomposition products, such as furfurals, cyclic ethers, and cracked lignin. The experimental results are shown in FIGS. 19 and 20. The Ru/C catalyst gives the highest yield of sorbitol. The addition of rhodium significantly improved the biomass conversion.

Example 9

A study was conducted on acid, base and metal functions of various catalysts and their ability to convert bagasse to desired compounds.

Zirconia catalysts were prepared by precipitation. A solution of $ZrOCl_2$ was added into ammonium hydroxide solution (pH=10-11). The precipitate was dried at 70° C. and then rinsed to remove chloride ions.

$WO_3/ZrO_2$ and $MgO/ZrO_2$ catalysts were prepared by incipient wetting impregnation. Appropriate amounts of precursors were dissolved in deionized water and evenly distributed onto the $ZrO_2$ supports. The wet catalysts were dried at 120° C. in oven for at least 12 hours. Some materials were calcined in air at 600° C. for up to 4 hours. The catalyst formulations that were tested are listed in Table 3 below.

TABLE 3

Catalyst Information

| Catalyst | Atomic Ratios | Metal Loading wt % | Note |
|---|---|---|---|
| Hydrous zirconia | — | — | Control |
| Tungstate zirconia | Wr:Zr = 0.053 | — | Acidity scoping |
| Tungstate zirconia | Wr:Zr = 0.106 | — | Acidity scoping |
| Magnesia zirconia | Mg:Zr = 0.037 | — | Basicity scoping |
| Magnesia zirconia | Mg:Zr = 10 | — | Basicity scoping |
| Rh loaded zirconia | — | 2.5% Rh | Control |
| Ni lodaded zirconia | — | 5% Ni | Control |
| NiB loaded zirconia | B:Ni = 0.037 | 5% Ni | Rh alternative |

All experiments were conducted using a 600 mL Parr reactor using ground sugarcane bagasse (<20 mesh) as the lignocellulosic biomass feed. The reactor was pre-pressurized with hydrogen at room temperature. The operation conditions were the same for all formulations and are shown in Table 4. Bagasse, catalyst, and the proper amount of water were co-filled in a Parr reactor and were well mixed by vigorous stirring (800 rpm) from the start of heating to the end of cooling. Aqueous and solid samples were taken after the deconstruction reaction was completed.

TABLE 4

Process conditions

| Bagasse weight [g] | Bagasse [wt %] | Catalyst Load [g] | Temp [° C.] | $H_2$ Pre-Charge Pressure [PSI] | Total Heating Time [min] | Total Retention Time [min] |
|---|---|---|---|---|---|---|
| 10.5 | 10 | 10 | 300 | 250 | 90 | 15 |

FIG. 20 shows the conversion of bagasse over the different catalysts. Among the screened catalysts, 2.5% Ru, 2.5% Rh/$ZrO_2$ catalyst gave the highest conversion of bagasse to non-solid components (~85%), while the conversion was lowest for 5% Ni/$ZrO_2$ (~69%), which was identical to the control experiment conversion when no catalyst was added. Using the hydrous $ZrO_2$ without any modification gave a conversion of ~76.5% suggesting that the Ni/$ZrO_2$ catalyst underwent rapid deactivation.

Two solid acid catalysts, 20% $WO_3/ZrO_2$ and 10% $WO_3/ZrO_2$, were tested resulting in bagasse conversions of 76% and 81%, respectively. Similarly, ~73% and ~80% conversion of bagasse were realized over two solid base catalysts, 1.2% $MgO/ZrO_2$ and 327% $MgO/ZrO_2$, respectively, indicating that the basicity of the catalyst also contributes to the biomass depolymerization. Again the 20% $WO_3/ZrO_2$ and 1.2% $MgO/ZrO_2$ had lower reactivity than the $ZrO_2$ support alone. This can be explained by the bifunctional nature of the hydrous $ZrO_2$, possessing acidic and basic sites, which both contribute to the catalytic deconstruction of bagasse. FIG. 20 also compares the bagasse conversion over 2.5% Rh/$ZrO_2$ with that over its alternative, 5% Ni, 0.34% B/$ZrO_2$ showing that the conversions are almost the same, ~82% for the two catalysts.

Carboxylic acids, sugars or polyols, and other oxygenates, including alcohols and hydroxyl ketones, are the main products that can be identified with current analytic capability. For the catalysts screened, the yields of total carboxylic acids are significantly higher than other aqueous products as shown in FIG. 21. Amongst the screened catalysts, 20% $WO_3/ZrO_2$ gave the highest acid yield, while 327% $MgO/ZrO_2$ gives the highest yield of the sugar/polyol products. Unidentified components comprise over 70% of the carbon in the aqueous products for each hydrolyzate, and these could be partially reduced polyols, large-molecular weight oligomers, lignin derivatives, etc. With such a large amount of unidentified components, it is difficult to determine how the different functionalities of the catalysts affect the bulk production distribution. However, it is hypothesized that a liquefied biomass product of comparable composition will be compatible with the downstream bioreforming process. A more detailed product distribution is shown in FIG. 22.

In summary, $WO_3$, MgO, and metal modified $ZrO_2$ catalysts with acid, base, and metal functions, respectively were tested for deconstruction of sugarcane bagasse. With appropriate formulations, more than 80% conversion can be obtained over 10% $WO_3/ZrO_2$, 327% $MgO/ZrO_2$, or 5% Ni, 0.34% $B/ZrO_2$ catalyst, suggesting each function including acid hydrolysis, base catalysis or metal hydrogenolysis can individually contribute to the lignocellulosic biomass deconstruction.

Example 10

This study was to validate the conversion of cellulose, hemicellulose and sugarcane bagasse using nickel-promoted tungsten carbide, to achieve high cellulose conversion and high polyols yield. Nickel-promoted tungsten carbide catalyst was prepared with the composition listed in Table 5.

TABLE 5

Composition of nickel-promoted tungsten carbide catalyst
Catalyst Composition

| Metal 1 | 2% Ni |
|---|---|
| Metal 2 | 30% $W_2C$ |
| Support | RX3 Extra Carbon |

Microcrystalline cellulose, ground sugarcane bagasse (<20 mesh) and hemicellulose (xylan) were used as representing cellulosic materials. All experiments were conducted using Parr reactor under a static $H_2$ atmosphere. The reaction temperature and residence time were major variables to be controlled. The reactor was pressurized with hydrogen to a desired pressure at room temperature prior to heating. The detailed experimental conditions are listed in Table 6.

TABLE 6

Conversion of cellulosic biomass using nickel tungsten carbide catalyst

| WC | Feedstock (Dry wt.) | Water (g) | Ni—$W_2C$/ AC (Dry wt. g) | $H_2$ Pressure (psi) | Temp (C.) | Time* (min) |
|---|---|---|---|---|---|---|
| 1 | 1 g MCC | 100 | 0.3 | 870 | 245 | 120 |
| 2 | 1 g Bagasse | 100 | 0.3 | 870 | 245 | 120 |
| 3 | 1 g Xylan | 100 | 0.3 | 870 | 245 | 120 |
| 4 | 10 g Bagasse | 100 | 1 | 870 | 245 | 120 |

*Total time includes 90 minutes heating time

FIGS. 23 and 24 show the overall results and product distribution of cellulosics conversion over nickel tungsten carbide catalyst. At low biomass concentration (1%), 95% of microcrystalline cellulose, 93% of hemicellulose and 78% of bagasse were converted to polyols, organic acids, and other sugar degradation products. The major products are ethylene glycol, propylene glycol and acetol. The high 60% ethylene glycol yield reported by Zhang and Chen was not achieved. This could be caused by different catalyst composition or larger scale reactor leading to different mass and heat transfer.

Pure carbohydrates gave higher yields of desired products as compared with bagasse. The detrimental effect of lignin, ash and/or extractives released from bagasse is observed in the bagasse runs. The used catalyst surface of the 10% bagasse run appeared to have a shiny coat, possibly due to glassified lignin or decomposition products.

FIG. 24 shows that sugars or polyols were decomposed to organic acids and other degradation products such as HMF and furfurals that are included in the unknowns.

Example 11

A study was conducted to show the ability of a variety of catalysts to liquefy a variety of types of biomass and to convert that biomass to a wide range of products including many highly deoxygenated products. Microcrystalline cellulose and corn stover were deconstructed using water, hydrogen, and various metals on oxide supports. All experiments were conducted under a static $H_2$ atmosphere. The detailed experimental conditions are listed in Table 7.

| WC | Feedstock (slurry 10 wt % solids) | Catalyst | $H_2$ Pressure (psi) | Temp (C.) | Time* (min) |
|---|---|---|---|---|---|
| 1 | Cellulose | 2% Pd 2% Ru, 8% W m-ZrO2 | 1250 | 300 | 100 |
| 2 | Corn Stover | 2% Pt 2% Re, m-ZrO2 | 1250 | 300 | 100 |
| 3 | Corn Stover | 2% Pd 0.5% Rh, m-ZrO2 | 1250 | 300 | 100 |
| 4 | Corn Stover | 2% Pd 2% Mo, W m-ZrO2 | 1250 | 300 | 100 |

*Total time includes 90 minutes heating time

FIG. 26 shows that 80 to 100% of the biomass feedstock was converted. FIG. 27 shows the deoxygenation levels from the catalytic deconstruction indicating promising selectivity to mono and poly-oxygenates. FIG. 28 shows the product yields of the deconstruction. FIG. 29 shows the overall conversion and the carbon that is converted in the aqueous phase.

Example 12

A study was conducted on the effect of hydrogen partial pressure on the deconstruction of microcrystalline cellulose using water, hydrogen and a metal oxide hydrodeoxygenation catalyst. (2% Pd 2% Ag/W—ZrO2)

A slurry having a concentration of 10 wt % solids in water was reacted for a 90 minute heating period at a temperature of 280° C. and varying starting partial pressures of hydrogen from 0 to 500 psi. All of the runs were pre-pressurized to the same level. Nitrogen was added as an inert for the runs with lower partial pressures of hydrogen in order to maintain the aqueous phase reaction of the cellulose.

FIGS. 30 and 31 show the ability of the catalysts to convert most of the cellulose to the aqueous phase and selectively to a wide range of products, many of which are highly deoxygenated. FIG. 30-B shows the amount of carbon put into the system from the cellulosic feed and converted into the aqueous phase. FIG. 32 shows the level of deoxygenation in the products at each of the varying partial pressures of hydrogen. The general trend observed shows that as hydrogen availability is increased, the deoxygenation increases and the amount of carbon converted into the aqueous phase increases.

Example 13

A study was conducted on the effect of temperature and hydrogen partial pressure on the deconstruction of loblolly pine and using water, hydrogen and a metal oxide hydrodeoxygenation catalyst. (2% Pd 2% Ag/W—ZrO2)

A slurry having a concentration of 10 wt % solids in water was reacted for a 90 minute heating period at varying temperatures of 240-300° C. and pressures of hydrogen from 1000-1450 psi. All of the runs were pre-pressurized to a level that would ensure the aqueous phase reaction of the lignocellulose.

Temperature plays a large role into the conversion of feedstock to products, particularly to oxygenates. More of the feedstock is converted with increased temperatures, but it is converted to a greater amount of unknown compounds. Increasing the reaction time decreases the amount of carbon that remains in the aqueous phase, indicating greater losses to the gas phase and degradation through condensation of products on the catalyst and reactor. FIGS. 33A and 33B show the mass and analytical balances and biomass conversion results of loblolly pine deconstruction at a variety of temperatures and pressures.

The invention claimed is:

1. A method of converting a biomass slurry to soluble oxygenated hydrocarbons, the method comprising:
   contacting solid biomass in an aqueous slurry with hydrogen and a heterogeneous deconstruction catalyst at a deconstruction temperature and a deconstruction pressure to produce a biomass hydrolysate that comprises ethylene glycol, propylene glycol, or xylitol,
   wherein the solid biomass comprises (a) lignin and (b) at least one of cellulose and hemicellulose, and wherein at least a portion of the soluble oxygenated hydrocarbons are derived from the lignin.

2. The method of claim 1 wherein the solid biomass is selected from the group consisting of an agricultural residue, wood material, an energy crop, and municipal solid waste.

3. The method of claim 1 wherein the heterogeneous deconstruction catalyst comprises an acidic resin or a basic resin.

4. The method of claim 1 wherein the heterogeneous deconstruction catalyst comprises a support and a member adhered to the support, wherein the member is selected from the group consisting of Cu, Fe, Ru, Ir, Co, Rh, Pt, Pd, Ni, W, Mo, alloys thereof, and combinations thereof.

5. The method of claim 4 wherein the heterogeneous deconstruction catalyst further comprises one or more members selected from the group consisting of Mn, Cr, B, V, Nb, Ta, Ti, Zr, Y, La, Sc, Zn, Cd, Ag, Au, Sn, Ge, P, Al, Ga, In, Tl, Ce, alloys thereof, and combinations thereof.

6. The method of claim 1 wherein the biomass hydrolysate comprises an additional member selected from the group consisting of alcohols, ketones, cyclic ethers, esters, carboxylic acids, aldehydes and a polyol.

7. The method of claim 1, wherein the aqueous slurry is produced by
   contacting a solid lignocellulosic biomass component with hot water in a hot water extraction process to yield the aqueous slurry and a liquid extract that comprises a soluble oxygenated hydrocarbon derived from the group consisting of hemicellulose and saccharides, wherein the aqueous slurry comprises the solid biomass; and
   separating the aqueous slurry from the liquid extract.

8. The method of claim 7 wherein the heterogeneous deconstruction catalyst comprises an acidic resin or a basic resin.

9. The method of claim 7 wherein the heterogeneous deconstruction catalyst comprises a support and a member adhered to the support, wherein the member is selected from the group consisting of Cu, Fe, Ru, Ir, Co, Rh, Pt, Pd, Ni, W, Mo, alloys thereof, and combinations thereof.

10. The method of claim 9 wherein the heterogeneous deconstruction catalyst further comprises one or more members selected from the group consisting of Mn, Cr, B, V, Nb, Ta, Ti, Zr, Y, La, Sc, Zn, Cd, Ag, Au, Sn, Ge, P, Al, Ga, In, Tl, Ce, alloys thereof, and combinations thereof.

11. The method of claim 7 wherein the deconstruction temperature is in a range of about 150° C. to 350° C.

12. The method of claim 7 wherein the deconstruction pressure is in a range of about 150 psi to 2000 psi.

13. The method of claim 7 wherein the biomass hydrolysate comprises an additional member selected from the group consisting of alcohols, ketones, cyclic ethers, esters, carboxylic acids, aldehydes and a polyol.

14. The method of claim 1, wherein the aqueous slurry is produced by:
   contacting a solid lignocellulosic biomass component with an organic solvent in an organosolv process to yield the aqueous slurry and a liquid extract that comprises a soluble oxygenated hydrocarbon derived from the group consisting of hemicellulose and saccharides, wherein the aqueous slurry comprises the solid biomass;
   separating the aqueous slurry from the liquid extract; and
   separating solvent from the liquid extract.

15. The method of claim 14 further comprising recycling the separated solvent back into the organosolv process.

16. The method of claim 14 wherein the heterogeneous deconstruction catalyst comprises an acidic resin.

17. The method of claim 14 wherein the heterogeneous deconstruction catalyst comprises a support and a member adhered to the support, wherein the member is selected from the group consisting of Cu, Fe, Ru, Ir, Co, Rh, Pt, Pd, Ni, W, Mo, alloys thereof, and combinations thereof.

18. The method of claim 17 wherein the heterogeneous deconstruction catalyst further comprises one or more members selected from the group consisting of Mn, Cr, B, V, Nb, Ta, Ti, Zr, Y, La, Sc, Zn, Cd, Ag, Au, Sn, Ge, P, Al, Ga, In, Tl, Ce, alloys thereof, and combinations thereof.

19. The method of claim 14 wherein the deconstruction temperature is in a range of about 80° C. to 350° C.

20. The method of claim 14 wherein the deconstruction pressure is in a range of about 100 psi to 2000 psi.

21. The method of claim 14 wherein the biomass hydrolysate further comprises an additional member selected from the group consisting of alcohols, ketones, cyclic ethers, esters, carboxylic acids, aldehydes and a polyol.

22. The method of claim 1, wherein the solid biomass is lignocellulose.

23. The method of claim 1, wherein the solid biomass is corn stover, straw, seed hulls, sugarcane leavings, bagasse, nutshells, cotton gin trash, manure, wood, bark, wood chips, sawdust, timber slash, mill scrap, recycled fiber, waste paper, yard clippings, poplar, willow, pine, switch grass, miscanthus, sorghum, alfalfa, prairie bluestream, corn, or soybeans.

24. The method of claim 7, wherein the solid lignocellulosic biomass component comprises (a) lignin and (b) at least one of cellulose and hemicellulose.

25. The method of claim 7, wherein the solid lignocellulosic biomass component is selected from the group consisting of an agricultural residue, a wood material, an energy crop, and municipal solid waste.

26. The method of claim 7, wherein the solid lignocellulosic biomass component is corn stover, straw, seed hulls, sugarcane leavings, bagasse, nutshells, cotton gin trash, manure, wood, bark, wood chips, sawdust, timber slash, mill scrap, recycled fiber, waste paper, yard clippings, poplar, willow, pine, switch grass, miscanthus, sorghum, alfalfa, prairie bluestream, corn, or soybeans.

27. The method of claim 14, wherein the solid lignocellulosic biomass component comprises (a) lignin and (b) at least one of cellulose and hemicellulose.

28. The method of claim 14, wherein the solid lignocellulosic biomass component is selected from the group consisting of an agricultural residue, a wood material, an energy crop, and municipal solid waste.

29. The method of claim 14, wherein the solid lignocellulosic biomass component is corn stover, straw, seed hulls, sugarcane leavings, bagasse, nutshells, cotton gin trash, manure, wood, bark, wood chips, sawdust, timber slash, mill scrap, recycled fiber, waste paper, yard clippings, poplar, willow, pine, switch grass, miscanthus, sorghum, alfalfa, prairie bluestream, corn, or soybeans.

30. The method of claim 7, wherein the aqueous slurry further comprises ash.

31. The method of claim 14, wherein the aqueous slurry further comprises ash.

* * * * *